US011099185B2

(12) United States Patent
Grus et al.

(10) Patent No.: US 11,099,185 B2
(45) Date of Patent: Aug. 24, 2021

(54) PREDICTIVE MARKERS USEFUL IN THE TREATMENT OF WET AGE-RELATED MACULAR DEGENERATION

(71) Applicant: maintect GmbH, Mainz (DE)

(72) Inventors: Franz Grus, Mainz (DE); Christina Korb, Mainz (DE); Norbert Pfeiffer, Mainz (DE)

(73) Assignee: maintect GmbH, Mainz (DE)

( * ) Notice: Subject to any disclaimer, the term of this patent is extended or adjusted under 35 U.S.C. 154(b) by 80 days.

(21) Appl. No.: 16/080,628

(22) PCT Filed: Feb. 28, 2017

(86) PCT No.: PCT/EP2017/054579
§ 371 (c)(1),
(2) Date: Aug. 28, 2018

(87) PCT Pub. No.: WO2017/148904
PCT Pub. Date: Sep. 8, 2017

(65) Prior Publication Data
US 2019/0072550 A1     Mar. 7, 2019

Related U.S. Application Data

(60) Provisional application No. 62/300,952, filed on Feb. 29, 2016.

(51) Int. Cl.
*G01N 33/564*     (2006.01)
*G01N 33/68*     (2006.01)

(52) U.S. Cl.
CPC ....... *G01N 33/564* (2013.01); *G01N 33/6854* (2013.01); *G01N 2800/164* (2013.01); *G01N 2800/52* (2013.01); *G01N 2800/56* (2013.01)

(58) Field of Classification Search
CPC ............. G01N 33/6854; G01N 33/564; G01N 2800/56; G01N 2800/164; G01N 2800/52
See application file for complete search history.

(56) References Cited

U.S. PATENT DOCUMENTS 7,344,846 B2 *   3/2008   Hageman ............. G01N 33/564
                                                                              435/7.21
2006/0079494 A1   4/2006   Santi et al.
2012/0264634 A1   10/2012   Amersdorfer et al.

FOREIGN PATENT DOCUMENTS

| EP | 1767546 A1 | 3/2007 |
| KR | 10-2012-0129023 A | 11/2012 |
| WO | 2010/060748 A1 | 6/2010 |
| WO | 2011/135067 A1 | 11/2011 |

OTHER PUBLICATIONS

Morohoshi et al. Autoantibody signature forage-related macular degeneration. Medical Research Archives 2015, Issue 3, pp. 1-16. (Year: 2015).*

(Continued)

*Primary Examiner* — Shafiqul Haq
(74) *Attorney, Agent, or Firm* — Larson & Anderson, LLC

(57) ABSTRACT

The invention is directed to the use of biomarkers to determine responsiveness of an individual with wet AMD to treatment with a VEGF antagonist, to diagnose and distinguish dry and wet AMD and to determine the risk of conversion of a dry AMD disease to a wet AMD disease.

11 Claims, 6 Drawing Sheets
Specification includes a Sequence Listing.

(56) References Cited

OTHER PUBLICATIONS

Morososhi et al. Autoantibody signature for age-related macular degeneration. Medical Research Archives 2015, Issue 3, pp. 1-16. (Year: 2015).*
Adamus, G. et al. "Autoantibodies against retinal proteins in paraneoplastic and autoimmune retinopathy", BMC Ophthalmology, 2004, pp. 19, vol. 4, No. 5.
Adamus, G. et al. "Prevalence of anti-retinal autoantibodies in different stages of Age-Related macular degeneration" BMC Ophthalmology, 2014, pp. 19, vol. 14, No. 1.
Dayhoff, M. et al. "A model of Evolutionary change in Proteins", Atlas of Protein Sequence and Structure, 1978, pp. 345-352.
Holash, J. et al. "VEGF-Trap: A VEGF blocker with Potent anti-tumor effects", PNAS, 2002, pp. 11393-11398, vol. 99, No. 17.
Iannaccone, A. et al. "Circulating Autoantibodies in Age-Related Macular Degeneration Recognize Human Macular Tissue Antigens Implicated in autophagy, Immunomodulation, and Protection from Oxidative Stress and Apoptosis", PLOS ONE, 2015, pp. 1-22.
Joachim, S. et al. "Analysis of IgG antibody patterns against retinal antigens and antibodies to ∝-crystallin, GFAP, and ∝-enolase in sera of patients with "wet" age-related macular degeneration" Graefe's Arch Clin Exp Ophthalmol., 2007, pp. 619-626, vol. 245, No. 5.
Kitchens, J. et al. "A pharmacogenetics study to predict outcome in patients receiving anti-VEGF therapy in age related macular degeneration" Clinical Ophthalmology, 2013, pp. 1987-1993, vol. 7.
Kruger Falk, M. et al. "Four-Year Treatment Results of Neovascular Age-Related Macular Degeneration with Ranibizumab and Causes for Discontinuation of Treatment" American Journal of Ophthalmology, 2013, pp. 89-95, vol. 155, No. 1.
Kubicka-Trzaska, A. et al. "Circulating anti-retinal antibodies in response to anti-angiogenic therapy in exudative age-related macular degeneration" Acta Ophthalmologica, 2014, pp. e610-e614, vol. 92, No. 8.
Li, T. et al. "KH906, a recombinant human VEGF receptor fusion protein, is a new effective topical treatment for corneal neovascularization", Molecular Vision, 2011, pp. 797-803, vol. 17.
Lorenz, K. et al. "Longitudinal Analysis of Serum Autoantibody-Reactivities in Patients with Primary Open Angle Glaucoma and Optic Disc Hemorrhage" PLOS One, 2016, pp. 1-13.
Morohosi, K. et al. "Serum autoantibody biomarkers for age-related macular degeneration and possible regulators of neovascularization" Experimental and Molecular Pathology, 2012, pp. 64-73, vol. 92, No. 1.
Morohosi, K. et al. "Identification of anti-retinal antibodies in patients with age-related macular degeneration", Experimental and Molecular Pathology, 2012, pp. 193-199, vol. 93, No. 2.
Okunuki, Y. et al. "Proteomic surveillance of retinal autoantigens in endogenous uveitis: implication of esterase D and brain-type creatine kinase as novel autoantigens" Molecular Vision, 2008, pp. 1094-1104, vol. 14.
Otsuji, T. et al. "Initial non-responders to ranibizumab in the treatment of age-related macular degeneration (AMD)", Clinical Ophthalmology, 2013, pp. 1487-1490, vol. 7.
Ren, G. et al. "Cellular targets of anti-∝-enolase autoantibodies of patients with autoimmune retinopathy", Journal of Autoimmunity, 2004, pp. 161-167. vol. 23.
Riley, G. et al. "Vascular Endothelial Growth Factor Trap in Non-Small Cell Lung Cancer", Clinical Cancer Research, 2007, p. 4623s-4627s, vol. 13.
Suzuki, M. et al. "Predictive factors for non-response to intravitreal ranibizumab treatment in age-related macular degeneration" Br J Ophtholmol. 2014, pp. 1186-1191, vol. 98.
Yafai, Y. et al. "Anti-angiogenic effects of the receptor tyrosine kinase inhibitor, pazopanib, on choroidal neovascularization in rats", European Jornal of Pharmacology, 2011, pp. 12-18, vol. 666, Nos. 1-3.

* cited by examiner

SEQUENCE LISTING

<160> NUMBER OF SEQ ID NOS: 3

<210> SEQ ID NO 1
<211> LENGTH: 431
<212> TYPE: PRT
<213> ORGANISM: Homo sapiens
<220> FEATURE:
<223> OTHER INFORMATION: recombinant sequence

<400> SEQUENCE: 1

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

-continued

```
Thr Lys Lys Asn Ser Thr Phe Val Arg Val His Glu Lys Asp Lys Thr
            195                 200                 205
His Thr Cys Pro Pro Cys Pro Ala Pro Glu Leu Leu Gly Gly Pro Ser
        210                 215                 220
Val Phe Leu Phe Pro Pro Lys Pro Lys Asp Thr Leu Met Ile Ser Arg
225                 230                 235                 240
Thr Pro Glu Val Thr Cys Val Val Val Asp Val Ser His Glu Asp Pro
                245                 250                 255
Glu Val Lys Phe Asn Trp Tyr Val Asp Gly Val Glu Val His Asn Ala
            260                 265                 270
Lys Thr Lys Pro Arg Glu Glu Gln Tyr Asn Ser Thr Tyr Arg Val Val
        275                 280                 285
Ser Val Leu Thr Val Leu His Gln Asp Trp Leu Asn Gly Lys Glu Tyr
290                 295                 300
Lys Cys Lys Val Ser Asn Lys Ala Leu Pro Ala Pro Ile Glu Lys Thr
305                 310                 315                 320
Ile Ser Lys Ala Lys Gly Gln Pro Arg Glu Pro Gln Val Tyr Thr Leu
                325                 330                 335
Pro Pro Ser Arg Asp Glu Leu Thr Lys Asn Gln Val Ser Leu Thr Cys
            340                 345                 350
Leu Val Lys Gly Phe Tyr Pro Ser Asp Ile Ala Val Glu Trp Glu Ser
        355                 360                 365
Asn Gly Gln Pro Glu Asn Asn Tyr Lys Thr Thr Pro Pro Val Leu Asp
370                 375                 380
Ser Asp Gly Ser Phe Phe Leu Tyr Ser Lys Leu Thr Val Asp Lys Ser
385                 390                 395                 400
Arg Trp Gln Gln Gly Asn Val Phe Ser Cys Ser Val Met His Glu Ala
                405                 410                 415
Leu His Asn His Tyr Thr Gln Lys Ser Leu Ser Leu Ser Pro Gly
            420                 425                 430

<210> SEQ ID NO 2
<211> LENGTH: 552
<212> TYPE: PRT
<213> ORGANISM: Homo sapiens
<220> FEATURE:
<223> OTHER INFORMATION: recombinant sequence

<400> SEQUENCE: 2

Met Val Ser Tyr Trp Asp Thr Gly Val Leu Leu Cys Ala Leu Leu Ser
1               5                   10                  15
Cys Leu Leu Leu Thr Gly Ser Ser Ser Gly Gly Arg Pro Phe Val Glu
            20                  25                  30
Met Tyr Ser Glu Ile Pro Glu Ile Ile His Met Thr Glu Gly Arg Glu
        35                  40                  45
Leu Val Ile Pro Cys Arg Val Thr Ser Pro Asn Ile Thr Val Thr Leu
    50                  55                  60
Lys Lys Phe Pro Leu Asp Thr Leu Ile Pro Asp Gly Lys Arg Ile Ile
65                  70                  75                  80
Trp Asp Ser Arg Lys Gly Phe Ile Ile Ser Asn Ala Thr Tyr Lys Glu
                85                  90                  95
Ile Gly Leu Leu Thr Cys Glu Ala Thr Val Asn Gly His Leu Tyr Lys
            100                 105                 110
Thr Asn Tyr Leu Thr His Arg Gln Thr Asn Thr Ile Ile Asp Val Val
        115                 120                 125
```

```
Leu Ser Pro Ser His Gly Ile Glu Leu Ser Val Gly Glu Lys Leu Val
    130                 135                 140
Leu Asn Cys Thr Ala Arg Thr Glu Leu Asn Val Gly Ile Asp Phe Asn
145                 150                 155                 160
Trp Glu Tyr Pro Ser Ser Lys His Gln His Lys Lys Leu Val Asn Arg
                165                 170                 175
Asp Leu Lys Thr Gln Ser Gly Ser Glu Met Lys Lys Phe Leu Ser Thr
            180                 185                 190
Leu Thr Ile Asp Gly Val Thr Arg Ser Asp Gln Gly Leu Tyr Thr Cys
        195                 200                 205
Ala Ala Ser Ser Gly Leu Met Thr Lys Lys Asn Ser Thr Phe Val Arg
    210                 215                 220
Val His Glu Lys Pro Phe Val Ala Phe Gly Ser Gly Met Glu Ser Leu
225                 230                 235                 240
Val Glu Ala Thr Val Gly Glu Arg Val Arg Leu Pro Ala Lys Tyr Leu
                245                 250                 255
Gly Tyr Pro Pro Pro Glu Ile Lys Trp Tyr Lys Asn Gly Ile Pro Leu
            260                 265                 270
Glu Ser Asn His Thr Ile Lys Ala Gly His Val Leu Thr Ile Met Glu
        275                 280                 285
Val Ser Glu Arg Asp Thr Gly Asn Tyr Thr Val Ile Leu Thr Asn Pro
    290                 295                 300
Ile Ser Lys Glu Lys Gln Ser His Val Val Ser Leu Val Val Tyr Val
305                 310                 315                 320
Pro Pro Gly Pro Gly Asp Lys Thr His Thr Cys Pro Leu Cys Pro Ala
                325                 330                 335
Pro Glu Leu Leu Gly Gly Pro Ser Val Phe Leu Phe Pro Pro Lys Pro
            340                 345                 350
Lys Asp Thr Leu Met Ile Ser Arg Thr Pro Glu Val Thr Cys Val Val
        355                 360                 365
Val Asp Val Ser His Glu Asp Pro Glu Val Lys Phe Asn Trp Tyr Val
    370                 375                 380
Asp Gly Val Glu Val His Asn Ala Lys Thr Lys Pro Arg Glu Glu Gln
385                 390                 395                 400
Tyr Asn Ser Thr Tyr Arg Val Val Ser Val Leu Thr Val Leu His Gln
                405                 410                 415
Asp Trp Leu Asn Gly Lys Glu Tyr Lys Cys Lys Val Ser Asn Lys Ala
            420                 425                 430
Leu Pro Ala Pro Ile Glu Lys Thr Ile Ser Lys Ala Lys Gly Gln Pro
        435                 440                 445
Arg Glu Pro Gln Val Tyr Thr Leu Pro Pro Ser Arg Asp Glu Leu Thr
    450                 455                 460
Lys Asn Gln Val Ser Leu Thr Cys Leu Val Lys Gly Phe Tyr Pro Ser
465                 470                 475                 480
Asp Ile Ala Val Glu Trp Glu Ser Asn Gly Gln Pro Glu Asn Asn Tyr
                485                 490                 495
Lys Ala Thr Pro Pro Val Leu Asp Ser Asp Gly Ser Phe Phe Leu Tyr
            500                 505                 510
Ser Lys Leu Thr Val Asp Lys Ser Arg Trp Gln Gln Gly Asn Val Phe
        515                 520                 525
Ser Cys Ser Val Met His Glu Ala Leu His Asn His Tyr Thr Gln Lys
    530                 535                 540
Ser Leu Ser Leu Ser Pro Gly Lys
```

```
545                 550

<210> SEQ ID NO 3
<211> LENGTH: 126
<212> TYPE: PRT
<213> ORGANISM: Homo sapiens
<220> FEATURE:
<223> OTHER INFORMATION: recmoninant sequence

<400> SEQUENCE: 3

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
            20                  25                  30

Ala Asp Ser Thr Gly Trp Thr Pro Leu His Leu Ala Val Pro Trp Gly
        35                  40                  45

His Leu Glu Ile Val Glu Val Leu Leu Lys Tyr Gly Ala Asp Val Asn
    50                  55                  60

Ala Lys Asp Phe Gln Gly Trp Thr Pro Leu His Leu Ala Ala Ala Ile
65                  70                  75                  80

Gly His Gln Glu Ile Val Glu Val Leu Leu Lys Asn Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Ala Ala
            115                 120                 125
```

PREDICTIVE MARKERS USEFUL IN THE TREATMENT OF WET AGE-RELATED MACULAR DEGENERATION

CROSS REFERENCES TO RELATED APPLICATIONS

This application claims the priority of U.S. provisional patent application 62/300,952, filed Feb. 29, 2016, the disclosure of which is incorporated herein by reference in its entirety.

TECHNICAL FIELD

This invention lies in the field of medical diagnostics and also of personalized therapy. The invention described herein can be utilized as a diagnostic assay to identify those subjects having dry or wet AMD. In a particular aspect, the invention is directed to predicting whether an individual having wet AMD will clinically respond to the treatment with a VEGF antagonist. Aspects of the invention further relate to additional diagnostic and prognostic methods regarding diagnosis and therapeutic treatment of the dry and wet AMD diseases.

BACKGROUND ART

Age-related macular degeneration (AMD) is the leading cause of blindness in elderly people in North America and Western Europe and has become a significant health problem as the percentage of individuals above the age of 50 increases (Hymann, Epidemiology, 1992). AMD targets the retinal pigment epithelium (RPE), a monolayer of cells between the light sensitive photoreceptors and the vascular choroid. As AMD progresses two distinct clinical manifestations of late AMD can develop and both forms can even occur in the same patient. One form is referred to as the dry or atrophic form, characterized by the accumulation of small drusen in the RPE leading to a loss of RPE and to a degeneration of the retina in the macular region. The dry form is more frequent (80% of AMD patients) and results in a mild loss of visual function. Its onset is less sudden and it occurs without coincident neovascularization. The more severe wet neovascular form is less common but causes approximately 80-90% of cases of serious loss of vision. The wet form is characterized by neovascular "membranes" derived from the choroidal vasculature that invade Bruch's membrane, leak, and often cause detachments of the RPE and or the neural retina. These new capillaries are abnormally permeable, allowing accumulation of serum and blood under the RPE and or the neurosensory retina. The leaking blood vessels lead to a scarring of the macula. The loss of vision in patients with wet AMD can be rapid and result in functional blindness. In patients with wet AMD the complex formed by the choroidal new vessels and the fibrous tissue can destroy the photoreceptors within 3-24 months. The dry form can turn into the wet form. Effective therapies for the dry AMD form are rare, whereas the wet form can be treated by laser photocoagulation, photodynamic therapy or by using VEGF antagonists. Early diagnosis of the wet form is essential in order to take action as promptly as possible to obtain best results from therapy. Anti-VEGF therapy is now used worldwide as the main therapy for treating wet AMD. Several VEGF antagonists for the treatment of wet AMD have been approved for human use, including ranibizumab (Lucentis®) and aflibercept (Eylea®).

A certain heterogeneity is seen with the implementation of anti-VEGF therapeutics and anti-VEGF therapy is not completely effective for every AMD patient. Some patients still lose their visual acuity despite treatment. This heterogeneity demonstrates the need for predictive biomarkers. It would be very helpful for AMD patients if the efficacy of the anti-VEGF treatment could be determined as early as possible in the treatment so that non-responders could change therapy or treatment regimen. Between 10-17% of eyes treated with intravitreal injections of ranibizumab were found to be non-responders (Otsuji et al, Clinical Ophthalmology, 2013; Suzuki et al., British Journal of Ophthalmology, 2014; Kruger Falk et al., American Journal of Ophthalmology 2013). The percentage of non-responders varies depending on the criteria and determination methods used. Earlier publication found even higher percentages of non-responders to anti-VEGF treatment. It was also reported that non-responders had initial clinical characteristics and certain risk factors such as prolonged AMD, previous photodynamic therapy, fibrovascular pigment epithelial detachment, lesion size, age of the patients.

No means are currently available to determine if a patient will respond positively to an anti-VEGF therapy. It was reported that candidate single nucleotide polymorphisms (SNP's) might serve as prognostic or predictive markers for AMD and a statistically significant association between the LOC387715 A69S TT genotype and anti-VEGF treatment outcome was found (Kitchens et al., Clinical Ophthalmology 2013). There is an increasing body of evidence that suggests a patient's genetic profile can be determinative to a patient's responsiveness to a therapeutic treatment. A determination of genetic factors that influence, for example, the response to a particular drug, could be used to provide a patient with a personalized treatment regimen. Such personalized treatment regimen offer the potential to maximize therapeutic benefit to the patient while minimizing related side effects that can be associated with alternative treatment regimen.

There is a need to identify factors which can be used to predict whether a wet AMD patient is likely to respond to a particular therapy. There is also a need to identify factors to diagnose dry and wet AMD, in particular to identify factors which distinguish between the two forms of AMD and furthermore there is a need to predict if a patient currently diagnosed with dry AMD will develop the wet form of the disease.

DISCLOSURE OF THE INVENTION

In a first aspect, the invention is directed to predicting whether an individual having wet AMD will clinically respond to the treatment with a VEGF antagonist. A second aspect of the invention relates to diagnose dry and wet AMD, in particular to factors which distinguish between the two forms of AMD. A third aspect, the invention is directed to predicting the risk of a patient with dry AMD disease to suffer from conversion of dry AMD to wet AMD.

A first aspect of the present invention is based on the finding that particular biomarkers can be used to select those individuals having wet AMD who are likely to respond to treatment with a VEGF antagonist. It was surprisingly found that the IgG autoantibody patterns in a sample from an individual having wet AMD compared to a control, can be used to predict whether that individual will respond to anti-VEGF treatment. The present invention thus allows a treatment provider to identify those individuals having wet AMD who are responders to anti-VEGF treatment, and those who are non-responders to such treatment, prior to administration of a VEGF antagonist and also during therapy with a VEGF antagonist.

These autoantibodies relevant for the first aspect of the invention, i.e. for the distinction between responders and non-responders to anti VEGF treatment, are for the purpose of this invention termed Group A antibodies. The Group A of antibodies consists of or includes antibodies directed against: mitogen-activated protein kinase 3 (MAPK3), opioid growth factor receptor (OGFR), PolyRp2, Chromosome 17 (open reading frame 56), eukaryotic initiation factor 4A-1 EIFA 4A-1), glutathione peroxidase 4 (GPX4), signal recognition particle 14 kDa protein (SRP14), Gamma-synuclein, histadine tRNA ligase (Jo-1), Pre-Albumin (transthyretin), glycerol-3-phosphate dehydrogenase (GPD2), AP-1 complex subunit mu-1 (AP1M1), alpha enolase (ENO1-H7), plasticity-related gene 2 (PRG2), ATP synthase, alliase GNB1-A3, tubulin beta-3 chain (TUBB3), heat shock protein 60 (HSP 60), islet cell autoantigen 1 (ICA1), selenoprotein O (SELO), superoxide dismutase (SOD), gamma-enolase (ENO2).

These Group A autoantibodies were additionally found to be useful in the prediction of the risk of conversion from dry AMD to a wet AMD disease.

Further aspects of the invention are based on the finding that IgG autoantibody patterns in a sample from an individual having wet AMD compared to a sample from an individual having dry AMD differ. Thus, a group of autoantibodies was identified which distinguishes between dry and wet AMD patients.

These autoantibodies relevant for the second aspect of the invention, i.e. for the distinction between dry and wet AMD, are for the purpose of this invention termed Group B antibodies. The Group B of antibodies consists of or includes antibodies directed against: alpha-synuclein, SELO, SPRY, GAPDH-H2, Annexin-V, THAP, VTI-B, HSP10, ESD, PKC80, ACO2-C2, OGFR, PBP-I2, CAZ-C3, EIFA1, MAPK3, ENO1-H7, Chromosome17, Aconitate Hydratase, GPX4.

Some of the autoantibodies of this invention are members of both the Group A and the Group B.

In a third aspect of the invention it was found, that members of the Group A and members of the Group B, i.e. autoantibodies which are members of either Group A or Group B and autoantibodies which are members of both Group A and Group B were additionally found to be useful in the prediction of the risk of conversion from dry AMD to a wet AMD disease.

The antibodies of Group A and Group B are assigned to the following subgroups relating to their diagnostic significance.

Regarding Group A:
a subgroup A-1 of first priority autoantibodies comprises MAPK3, OGFR, SRP14, ENO2, SOD, Pre-Albumin, Jo-1, PolyRp2, Chromosome 17, EIFA1;
a subgroup A-2 of second priority autoantibodies comprises GPX4, Gamma-synuclein, GPD2, AP1M1, ENO1-H7, PRG2;
a subgroup A-3 of third priority autoantibodies comprises ATP synthase, GNB1-A3, TUBB3, HSP60, ICA1, SELO.

Regarding Group B:
a subgroup B-1 of first priority autoantibodies comprises alpha-synuclein, SELO, SPRY, GAPDH-H2, Annexin-V, THAP, VTI-B, HSP10;
a subgroup B-2 of second priority autoantibodies comprises ESD, PKC80, ACO2-C2, OGFR, PBP-I2, CAZ-C3, EIFA1, MAPK3;
a subgroup B-3 of third priority autoantibodies comprises ENO1-H7, Chromosome17, Aconitate Hydratase, GPX4.

As will be evident from the text below, in various embodiments of the different aspects of the invention, one or several autoantibodies of a specified group or subgroup is relevant to a particular step of a method of diagnosis or prognosis relating to AMD. For the purpose of this invention the phrase one or several antibodies selected from antibodies of a group or of a subgroup, in particular directed against a list of specified antigenic proteins, comprises each of the autoantibodies of the specified group or subgroup—or each of the corresponding antigenic proteins—separately and in all possible combinations with one or more than one up to all of the other antibodies or antigens of the particular group or subgroup of antibodies or antigens. Thus, conversely, it is understood that the phrase one or several antibodies selected from antibodies of a particular group or subgroup may include each and every one of the antibodies listed as member of the particular group or subgroup or may include any fraction thereof, e.g. the all of the members except for one or more than one of the antibodies belonging to a particular group.

For the purpose of this invention, unless otherwise explicitly stated or unless evident from the context, the terms diagnosis and diagnostic relate to the diagnosis of dry and wet AMD and also to the prognosis of a prospective course of dry and wet AMD, including but not limited to responsiveness to a particular AMD treatment, in particular a treatment of wet AMD with a VEGF-antagonist, and in particular to the risk of conversion from dry to wet AMD.

For the purpose of this invention, the terms autoantibodies, antibodies and immunoglobulins shall be used interchangeably. An autoantibody is an antibody formed in response to, and reacting against, an antigenic constituent of the individual's own tissue. An autoantibody is directed against one or more of the individual's own protein (self antigen).

In one embodiment, of the first aspect of the invention a method for determining the responsiveness of an individual with wet AMD to treatment with a VEGF antagonist is provided.

In one embodiment of the first aspect of the invention a method for determining the responsiveness of an individual with wet AMD to treatment with a VEGF antagonist by measuring the autoantibody content of a sample from said individual and comparing it with the antibody content of a healthy control is provided.

In one embodiment, the invention provides a method of determining the responsiveness of an individual with wet AMD to treatment with a VEGF antagonist, the method comprising:
(i) isolating a sample from an individual having wet AMD;
(ii) determining the quantity of one or several antibodies selected from Group A antibodies directed against MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1, SELO, SOD, ENO2 and
(iii) assigning the individual as a VEGF antagonist responder if the sample has an increased or decreased level of any one of the Group A antibodies MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1, SELO, SOD, ENO2 antibodies compared to a control value, in particular a control value derived from healthy subjects and/or from AMD patients who are responders and/or who are non-responders to treatment with a VEGF antagonist.

In a preferred embodiment, the invention in the first aspect provides a method of determining the responsiveness of an individual with wet AMD to treatment with a VEGF antagonist, the method comprising:
(i) isolating a sample from an individual having wet AMD;
(ii) determining the quantity of antibodies directed against selected from a subgroup A-1 of antibodies directed against MAPK3, OGFR, SRP14, ENO2, SOD, Pre-Albumin, Jo-1, PolyRp2, Chromosome 17, EIFA1; and
(iii) assigning the individual as a VEGF antagonist responder if the sample has an increased or decreased level of antibodies used in step 2 compared to a control value, in particular a control value derived from healthy subjects and/or from AMD patients who are responders and/or who are non-responders to treatment with a VEGF antagonist.

In another embodiment of the invention there is provided a method for determining whether a subject with wet AMD should be treated with a VEGF antagonist, the method comprising:
(a) isolating a sample from the subject;
(b) determining the quantity of one or several antibodies selected from antibodies directed against MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1, SELO, SOD, ENO2 in the sample; and
(c) determining that the subject should be treated with a VEGF antagonist.

In a preferred embodiment of the invention there is provided a method for determining whether a subject with wet AMD should be treated with a VEGF antagonist, the method comprising:
(a) isolating a sample from the subject;
(b) determining the quantity of antibodies directed against selected from a subgroup A-1 of antibodies directed against MAPK3, OGFR, SRP14, ENO2, SOD, Pre-Albumin, Jo-1, PolyRp2, Chromosome 17, EIFA1 in the sample; and
(c) determining that the subject should be treated with a VEGF antagonist.

In these and other embodiments of the invention in the method provided for determining whether a subject with wet AMD should be treated with a VEGF antagonist, said subject should be treated with a VEGF antagonist, when the level of one or several group A autoantibodies in the sample is increased or decreased by at least 10%, by 20%, by 30%, by 40%, by 50%, by 100%, by 150%, by 200%, by 250%, preferably by 25%-150%, more preferably by 50-100%, in the sample compared to a control value, in particular a control value derived from healthy subjects.

In some embodiments of the invention the determination of the quantity of antibodies may be done using Western blot or immunoblot assays, enzyme-linked immunoabsorbent assays (ELISA), radioimmunoassays, real-time PCR, microarrays, lateral flow, microfluidic, bead based assays, mass spectrometry.

In some embodiments of the invention for the determination of the quantity of antibodies the binding partners are not limited to their physiological antigenic binding partners but include also e.g. peptides such as fragments of the entire physiological polypeptide or other variants thereof.

In some embodiments of the invention including the method for determining whether a subject with wet AMD should be treated with a VEGF antagonist, the method can be performed with a sample that is a fluid sample such as blood, serum, tears, saliva, urine, a cell sample such as buccal cells, aqueous humor or vitreous body of the eye.

In some embodiments of the first aspect of the invention a kit for determining an AMD patient as a responder to anti-VEGF treatment is provided.

In some embodiments of the invention a diagnostic kit for determining if an individual with wet AMD is a VEGF antagonist responder is provided, the kit comprises one or more than one agent for measuring the quantity of one or several autoantibodies selected from Group A antibodies directed against MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1, SELO, SOD, ENO2 and instructions for use or in particular for measuring the quantity of one or several autoantibodies selected from subgroup A-1 and or subgroup A-2 and/or subgroup A-3.

In another embodiment a diagnostic kit for determining if an individual with wet AMD is a VEGF antagonist responder is provided, the kit comprises antigen carrying elements which carry ocular antigens and/or carries one or several antigens of any of Groups A and/or B. An ocular antigen is defined as an antigen expressed in any tissue of the eye.

In some embodiments the antigen carrying element is or is part of a microarray slide, such as a lateral flow test strip or a microfluidic chip. In further embodiments such a diagnostic kit comprises auxiliary materials such as analytical tools and or software for an image reader wherein the software is used for one or more of the steps of quantifying the measured autoimmune reactivity. In further embodiments auxiliary material for taking a sample of body fluid is included, such as for example blotting paper, reactants and/or reaction containers for the detection and measurement of the autoimmune reactivity after incubation of the antigen carrying element with a body fluid or reactants for treating a body fluid sample prior to incubation with the antigen carrying element or for eluting the body fluid from an adsorbant material on which it was collected.

The second aspect of the invention relates to a method to diagnose wet and dry AMD and to distinguish between the two forms of the AMD disease based on a Group of autoantibodies termed the Group B of antibodies as mentioned above. While the dry form is more frequent and less severe, patients with dry AMD have an increased risk of developing the more severe form of wet AMD. Thus, in the second aspect of the invention autoimmunereactivites distinctive for dry and wet AMD are analyzed. In particular the amount of the Group B antibodies are compared between a sample from an individual to be tested and control values which may be obtained by analysis of the autoimmunereactivities of the same Group B antibodies from healthy individuals and/or from individuals with dry AMD and/or with individuals with wet AMD.

In one embodiment of the second aspect of the invention a method is provided to determine whether an individual suffers from dry AMD and/or wet AMD, the method comprising:
isolating a sample from a subject;
determining the quantity of one or several antibodies selected from Group B antibodies directed against alpha-synuclein, SELO, SPRY, GAPDH-H2, Annexin-V, THAP, VTI-B, HSP10, ESD, PKC80, ACO2-C2, OGFR, PBP-I2, CAZ-C3, EIFA1, MAPK3, ENO1-H7, Chromosome17, Aconitate Hydratase, GPX4 and determining that the individual suffers from the dry and/or the wet AMD disease if the amount of the selected Group B autoantibodies is increased or decreased, in particular increased or decreased by at least 20%, at least 30%, at least 40%, at least 50% or at least 75% compared to control values, in particular control values derived from subjects who are healthy and/or derived from subjects with dry AMD and/or with wet AMD.

In a preferred embodiment a method for diagnosis of wet and dry AMD and for distinguishing between the two forms of the AMD is provided, the method comprising:

isolating a sample from a subject;

determining the quantity of one or several antibodies of a subgroup B-1 of the Group B autoantibodies directed against alpha-synuclein, SELO, SPRY, GAPDH-H2, Annexin-V, THAP, VTI-B, HSP10;

determining that the individual suffers from the dry and/or the wet AMD disease if the amount of the selected Group B autoantibodies is increased or decreased, in particular increased or decreased by at least 20%, at least 30%, at least 40%, at least 50% or at least 75%, compared to a control value, in particular control values.

In the third aspect of the invention a method is provided to determine the probability that a patient diagnosed with dry AMD will develop wet AMD. Autoantibodies which are members of the Group A and autoantibodies which are members of the Group B, i.e. autoantibodies which are members of either Group A or of Group B and autoantibodies which are members of both Groups A and B were found to be useful in the prediction of the risk of conversion from dry AMD to a wet AMD disease.

In one embodiment of the third aspect of the invention a method is provided to determine that an individual with dry AMD is at risk to develop wet AMD, the method comprising:

isolating a sample from a subject;

determining the quantity of one or several antibodies selected from autoantibodies which are members of Group A or of Group B wherein Group A antibodies are directed against MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1, SELO, SOD, ENO2 and wherein Group B antibodies are directed against alpha-synuclein, SELO, SPRY, GAPDH-H2, Annexin-V, THAP, VTI-B, HSP10, ESD, PKC80, ACO2-C2, OGFR, PBP-I2, CAZ-C3, EIFA1, MAPK3, ENO1-H7, Chromosome17, Aconitate Hydratase, GPX4 determining that the individual is at risk to develop wet AMD if the amount of the selected antibodies is decreased or increased, in particular decreased or increased by at least 20%, at least 30%, at least 40%, at least 50%, or at least 75% compared to control values, in particular control values derived from subjects who are healthy and/or derived from subjects with dry AMD and/or with wet AMD.

In one embodiment of the third aspect of the invention a method is provided to determine that an individual with dry AMD is at risk to develop wet AMD, the method comprising:

isolating a sample from a subject;

determining the quantity of one or several antibodies selected from autoantibodies which are members of preferred subgroups A-1 and/or B-1 of Groups A and B, wherein antibodies of the subgroup A-1 are directed against MAPK3, OGFR, SRP14, ENO2, SOD, Pre-Albumin, Jo-1, PolyRp2, Chromosome 17, EIFA1; and wherein antibodies of subgroup B-1 are directed against alpha-synuclein, SELO, SPRY, GAPDH-H2, Annexin-V, THAP, VTI-B, HSP10;

determining that the individual is at risk to develop wet AMD if the amount of the selected antibodies is decreased or increased, in particular decreased or increased by at least 20%, at least 30%, at least 40%, at least 50%, or at least 75% compared to control values, in particular control values derived from subjects who are healthy and/or derived from subjects with dry AMD and/or with wet AMD.

In some of these and other embodiments of the third aspect of the invention a method is provided to determine that an individual with dry AMD is at risk to develop wet AMD, the method comprising:

isolating a first sample from a subject;

isolating a second sample from the subject within a time period of about 2 weeks, or of about 1 month, or of about 2 months, or of about 6 months, or of about 12 months, or of at least about 12 months after the first sample;

determining the amount of one or several selected antibodies from Group A or from Group B or sub-groups of them as described above.

determining that the individual is at risk to develop wet AMD if the amount of the selected antibodies is decreased or increased in the second sample compared to the first sample, in particular decreased or increased by at least 20%, at least 30%, at least 40%, at least 50%, or at least 75%.

BRIEF DESCRIPTION OF THE DRAWINGS

The invention will be better understood and objects other than those set forth above will become apparent when consideration is given to the following detailed description thereof. This description makes reference to the annexed figures, wherein.

DETAILED DESCRIPTION OF THE INVENTION

Figure 1:
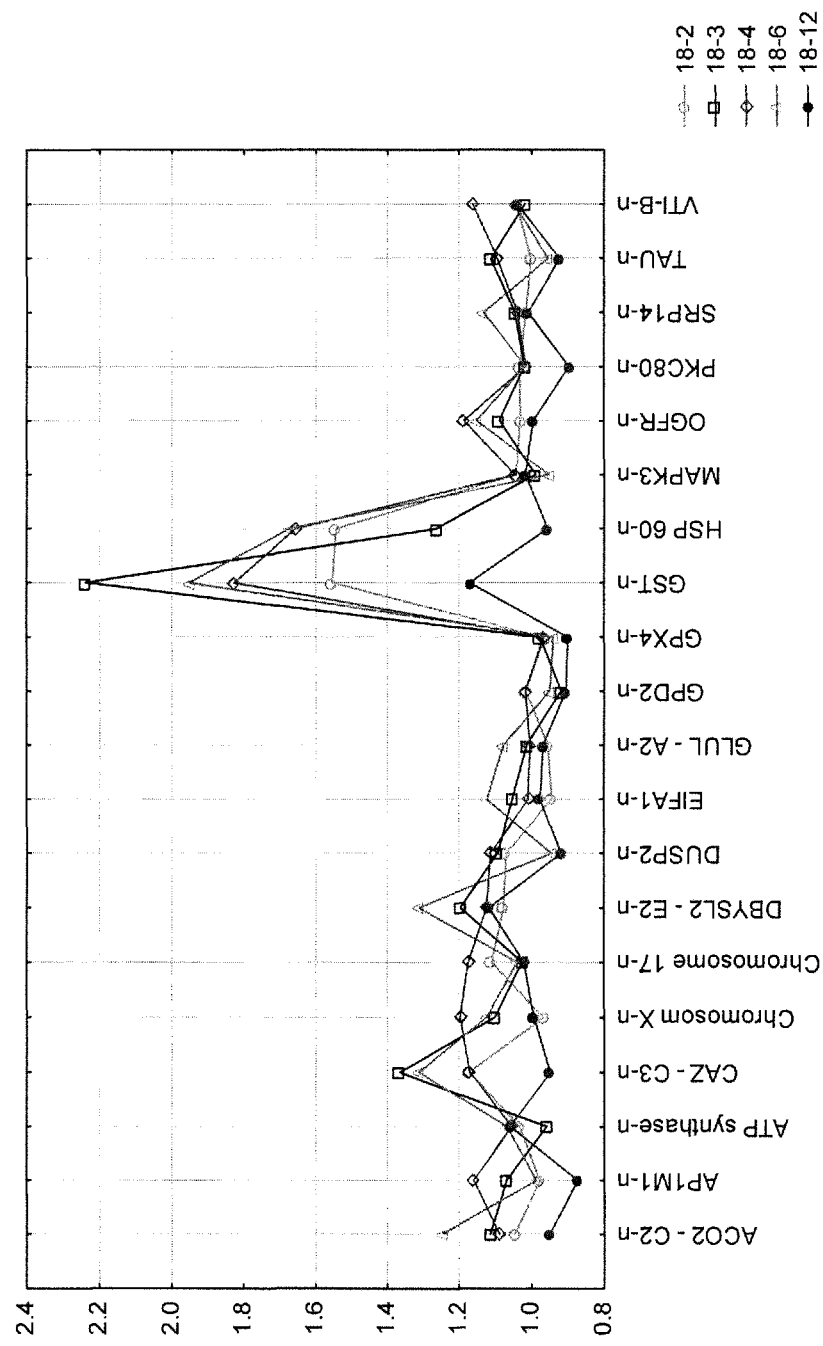
FIG. 1 shows a longitudinal analysis of IgG immunoreactivities in wet AMD patients, who started with Lucentis treatment. Samples were taken before and 2, 3, 4, 6, and 12 months after starting Lucentis treatment.
Figure 2:
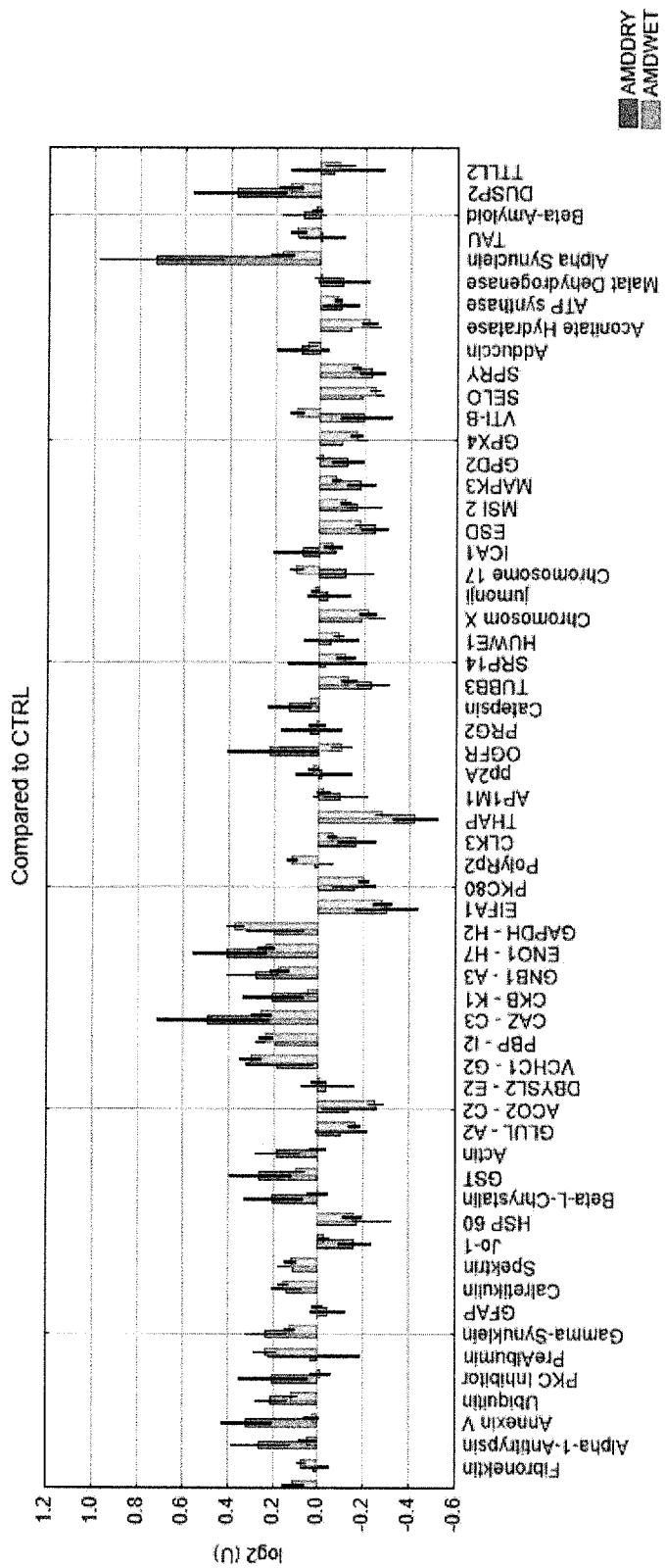
FIG. 2: Comparison of immunoreactivities in patients suffering from dry AMD and wet AMD compared to CTRL. All immunoreactivities.
Figure 3:
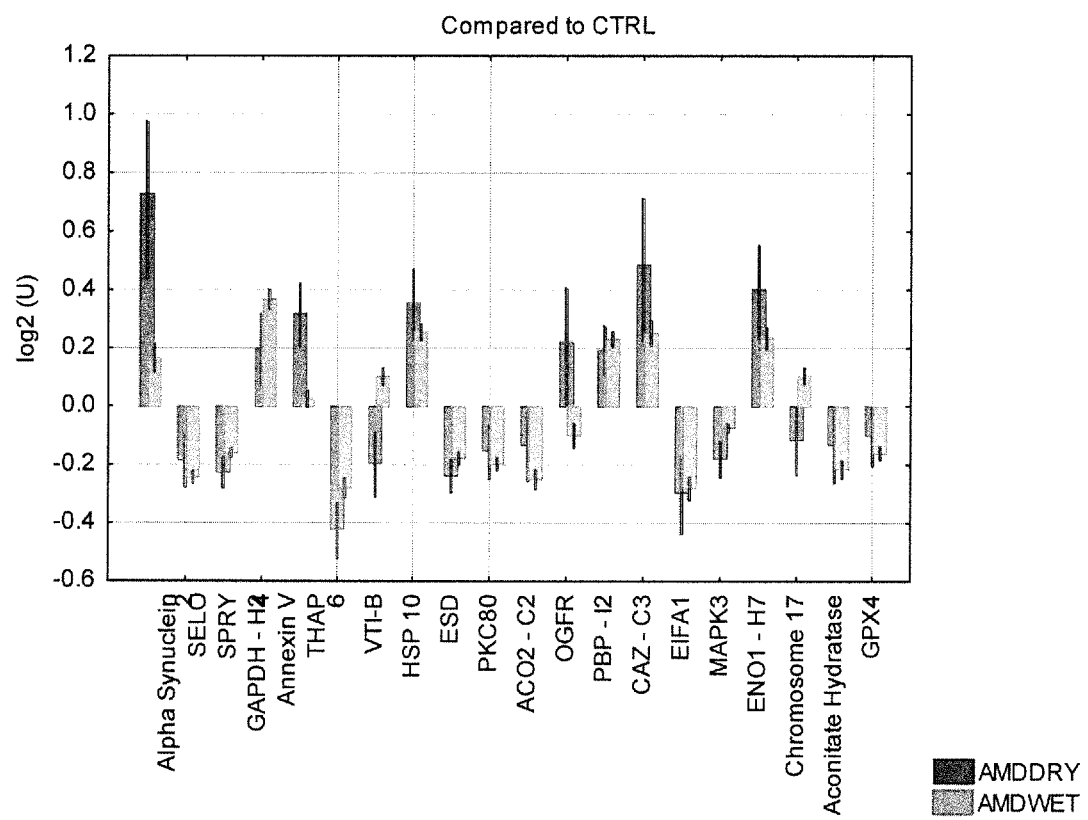
FIG. 3: Comparison of immunoreactivities in patients suffering from dry AMD and wet AMD compared to CTRL. 20 most significant reactivities.

Good results can be achieved for many patients suffering from wet AMD when treated with the approved VEGF antagonists (ranibizumab, aflibercept), meaning either a gain of vision or at least stability of the visual acuity. However, there exists still a certain percentage of patients which do not respond to those approved therapies. These patients suffer from further vision loss and are so called non-responders.

A patient can be considered a responder if treatment with a VEGF antagonist is useful and effective, as regards not only improvement but also stability, meaning a visual acuity (VA) loss of fewer than 15 ETDRS letters (ETDRS stands for Early Treatment Diabetic Retinopathy Study) after three successive follow-up visits (the follow-up visits start after three anti-VEGF injections). A patient can be considered as responder who gains visual acuity and maintains the gain over time. Patients who gain visual acuity but do not maintain the gain, losing visual acuity to not lower than at baseline are also considered responders. Responders are also considered as patients who gain visual acuity but do not maintain the gain, losing visual acuity to less than 15 ETDRS letters lower than at baseline. Patients who do not gain visual acuity but remain stable, with visual acuity loss not lower than at baseline are also considered as responders. Patients who do not gain visual acuity but whose visual acuity loss does not exceed 15 ETDRS letters compared to a baseline are also considered as responders.

A patient can be considered a non-responder if treatment with a VEGF antagonist gives no overall clinical benefit, assessed on the basis of morphological and functional parameters, and there is immediate or late visual loss. Non-responders are patients who lose more than 15 ETDRS letters in total in three successive follow-up visits (the follow-up visits start after three anti-VEGF injections). Non-responders are also considered as patients who lose more than 30 ETDRS letters compared with baseline and or best visual acuity recorded at baseline. Non-responders are also defined as patients whose best corrected visual acuity (BCVA) had worsened in the logMAR score. Besides the functional definitions, non-responders are also determined by fundus findings including OCT (optical coherence tomography). A non-responder is also defined as a patient in whom exudative fundus findings (pigment epithelial detachment, subretinal fluid, macular oedema, haemorrhage) had increased or had appeared after treatment, or in whom the central retinal thickness (CTR) increased by more than 100 μm within 12 months after the initial anti-VEGF injection.

It is known that two third of serum immunoglobulins in healthy individuals are natural occurring autoantibodies. The autoantibody patterns of patients suffering from wet and/or suffering from dry AMD and the autoantibody patterns of patients suffering from wet AMD receiving VEGF antagonist therapy were analysed.

It was surprisingly found that the amount of autoantibodies directed against antibodies of Group A comprising MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1 and SELO, SOD, ENO2 is significantly different in the serum of patients suffering from either dry or wet AMD in comparison to healthy patients. The quantity of one or several autoantibodies selected from autoantibodies directed against MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1 and SELO, SOD, ENO2 in the patient serum can therefore be used as a means to determine if a patient suffering from dry or wet AMD will respond to a VEGF antagonist therapy, before the VEGF antagonist therapy is initiated.

It was also found that in wet AMD patients with vision gain after ranibizumab therapy the serum level of antibodies directed against OGFR, Gamma-synuclein, Pre-Albumin and PRG2 were significantly increased, whereas in patients who showed a vision loss after ranibizumab therapy the level of said antibodies was significantly decreased.

Furthermore, e.g. immunoreactivities against PolyRp2, GNB1-A3, and TUBB3 are down-regulated in patients improving vision during 12 months under Lucentis treatment and upregulated in those who do not.

The detectable amount of autoantibodies in the serum of a patient suffering from wet AMD changes over time. A positive correlation between an optimal dosing regimen and the level of autoantibodies could have been identified. The quantity of one or several autoantibodies selected from the Group A of autoantibodies directed against MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1 and SELO, SOD, ENO2 is therefore also a predictive marker when the VEGF antagonist needs to be applied to the patient.

Surprisingly it was also found, that autoantibody patterns are able to differentiate between patients suffering from wet or dry AMD. In particular, changes in the autoantibody levels of one or several autoantibodies selected from autoantibodies of Group B of autoantibodies directed against alpha-synuclein, SELO, SPRY, GAPDH-H2, Annexin-V, THAP, VTI-B, HSP10, ESD, PKC80, ACO2-C2, OGFR, PBP-I2, CAZ-C3, EIFA1, MAPK3, ENO1-H7, Chromosome17, Aconitate Hydratase, GPX4.

Furthermore, it was found that changes in the autoantibody levels of one or several autoantibodies selected from autoantibodies of Group A or of Group B as defined above directed have a prognostic value to indicate the conversion of the dry AMD form to the wet AMD form.

VEGF is a well-characterised signal protein which stimulates angiogenesis. A "VEGF antagonist" refers to a molecule capable of neutralizing, blocking, inhibiting, abrogating, reducing or interfering with VEGF activities including its binding to one or more VEGF receptors. The VEGF antagonist may be administered intravitreally, e.g. through injection, or topically, e.g. in form of eye drops. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases, and fusions proteins. The invention also provides non-antibody VEGF antagonists.

a) Antibody VEGF Antagonists

In one embodiment, the VEGF antagonist is an antibody. In one embodiment, the VEGF antagonist is a mimetic of the VEGF receptor. In one embodiment, the VEGF antagonist is ranibizumab. In one embodiment, the VEGF antagonist is bevacizumab.

b) Non-Antibody VEGF Antagonists

In one embodiment, the VEGF antagonist is a non-antibody VEGF antagonist. In one aspect of the invention, the non-antibody VEGF antagonist is an immunoadhesin. One such immuoadhesin is aflibercept (Eylea®), which has recently been approved for human use and is also known as VEGF-trap (Holash et al., PNAS USA, 2002; Riely & Miller, Clinical Cancer Research, 2007). Aflibercept is the preferred non-antibody VEGF antagonist for use with the invention. Aflibercept is a recombinant human soluble VEGF receptor fusion protein consisting of portions of human VEGF receptors 1 and 2 extracellular domains fused to the Fc portion of human IgG1. It is a dimeric glycoprotein with a protein molecular weight of 97 kilodaltons (kDa) and contains glycosylation, constituting an additional 15% of the total molecular mass, resulting in a total molecular weight of 115 kDa. It is conveniently produced as a glycoprotein by expression in recombinant CHO K1 cells. Each monomer can have the following amino acid sequence (SEQ ID NO: 1):

```
SDTGRPFVEMYSEIPEIIHMTEGRELVIPCRVTSPNITVTLKKFP

LDTLIPDGKRIIWDSRKGFIISNATYKEIGLLTCEATVNGHLYKTNYLTH

RQTNTIIDVVLSPSHGIELSVGEKLVLNCTARTELNVGIDFNWEYPSSKH

QHKKLVNRDLKTQSGSEMKKFLSTLTIDGVTRSDQGLYTCAASSGLMTKK

NSTFVRVHEKDKTHTCPPCPAPELLGGPSVFLFPPKPKDTLMISRTPEVT

CVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELTK

NQVSLTCLVKGFYPSDIAVEWESNGQPENNYKTTPPVLDSDGSFFLYSKL

TVDKSRWQQGNVFSCSVMHEALHNHYTQKSLSLSPG
``` and disulfide bridges can be formed between residues 30-79, 124-185, 246-306 and 352-410 within each monomer, and between residues 211-211 and 214-214 between the monomers.

Another non-antibody VEGF antagonist immunoadhesin currently in pre-clinical development is a recombinant human soluble VEGF receptor fusion protein similar to VEGF-trap containing extracellular ligand-binding domains 3 and 4 from VEGFR2/KDR, and domain 2 from VEGFR1/Flt-1; these domains are fused to a human IgG Fc protein fragment (Li et al., Molecular Vision, 2011). This antagonist binds to isoforms VEGF-A, VEGF-B and VEGF-C. The molecule is prepared using two different production processes resulting in different glycosylation patterns on the final proteins. The two glycoforms are referred to as KH902 (conbercept) and KH906. The fusion protein can have the following amino acid sequence (SEQ ID NO:2):

```
MVSYWDTGVLLCALLSCLLLTGSSSGGRPFVEMYSEIPEIIHMTE

GRELVIPCRVTSPNITVTLKKFPLDTLIPDGKRIIWDSRKGFIISNATYK

EIGLLTCEATVNGHLYKTNYLTHRQTNTIIDVVLSPSHGIELSVGEKLVL

NCTARTELNVGIDFNWEYPSSKHQHKKLVNRDLKTQSGSEMKKFLSTLTI

DGVTRSDQGLYTCAASSGLMTKKNSTFVRVHEKPFVAFGSGMESLVEATV

GERVRLPAKYLGYPPPEIKWYKNGIPLESNHTIKAGHVLTIMEVSERDTG

NYTVILTNPISKEKQSHVVSLVVYVPPGPGDKTHTCPLCPAPELLGGPSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENN

YKATPPVLDSDGSFFLYSKLTVDKSRWQQGNVFSCSVMHEALHNHYTQKS

LSLSPGK
``` and, like VEGF-trap, can be present as a dimer. This fusion protein and related molecules are further characterized in EP1767546.

Other non-antibody VEGF antagonists include antibody mimetics (e.g. Affibody® molecules, affilins, affitins, anticalins, avimers, Kunitz domain peptides, and monobodies) with VEGF antagonist activity. This includes recombinant binding proteins comprising an ankyrin repeat domain that binds VEGF-A and prevents it from binding to VEGFR-2. One example for such a molecule is DARPin® MP0112. The ankyrin binding domain may have the following amino acid sequence (SEQ ID NO: 3):

```
GSDLGKKLLEAARAGQDDEVRILMANGADVNTADSTGWTPLHLAV
PWGHLEIVEVLLKYGADVNAKDFQGWTPLHLAAAIGHQEIVEVLLKNGAD
VNAQDKFGKTAFDISIDNGNEDLAEILQKAA
```

Recombinant binding proteins comprising an ankyrin repeat domain that binds VEGF-A and prevents it from binding to VEGFR-2 are described in more detail in WO2010/060748 and WO2011/135067.

Further specific antibody mimetics with VEGF antagonist activity are the 40 kD pegylated anticalin PRS-050 and the monobody angiocept (CT-322).

The non-antibody VEGF antagonist may be modified to further improve its pharmacokinetic properties or bioavailability. For example, a non-antibody VEGF antagonist may be chemically modified (e.g., pegylated) to extend its in vivo half-life. Alternatively or in addition, it may be modified by glycosylation or the addition of further glycosylation sites not present in the protein sequence of the natural protein from which the VEGF antagonist was derived.

Variants of the above-specified VEGF antagonists that have improved characteristics for the desired application may be produced by the addition or deletion of amino acids. Ordinarily, these amino acid sequence variants will have an amino acid sequence having at least 60% amino acid sequence identity with the amino acid sequences of SEQ ID NO: 1, SEQ ID NO: 2 or SEQ ID NO: 3, preferably at least 80%, more preferably at least 85%, more preferably at least 90%, and most preferably at least 95%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with SEQ ID NO: 1, SEQ ID NO: 2 or SEQ ID NO: 3, after aligning the sequences and introducing gaps, if necessary, to achieve the maximum percent sequence identity, and not considering any conservative substitutions as part of the sequence identity.

Sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences.

The autoantibody pattern, the presence or lack of a certain quantity of an antibody in a sample from an individual having AMD can individually, or in combination, serve as biomarkers to predict responsiveness of that individual to treatment with a VEGF antagonist. The presence of these biomarkers can be determined in a sample from an individual of interest. The sample can be any sample including but is not limited to a fluid sample such as blood, serum, tears, saliva, urine, a cell sample such as buccal cells, aqueous humor or vitreous body of the eye.

As used herein, "predicting" indicates that the methods described herein provide information to enable a health care provider to determine the likelihood that an individual having wet AMD will respond to VEGF antagonist treatment (anti-VEGF therapy). Following a positive determination of the relevant biomarker(s) in a sample of interest, the individual will be administered a VEGF antagonist.

To determine the levels of autoantibodies any known method in the art can be used. Methods to quantify the autoantibody contents include but are not limited to standard immunological analytical techniques such as Western blot or immunoblot assays, enzyme-linked immunoabsorbent assays (ELISA), radioimmunoassays, real-time PCR, microarrays, lateral flow, microfluidic assays, bead based assays, nontargeted proteomics involving e.g. mass-analyzers such as ion-trap detection, Fourier transform-ion cyclotron resonance, time-of-flight (TOF) mass spectrometry, targeted proteomics involving e.g. the use of selected reaction monitoring (SRM) with triple quadrupole mass spectrometry (TQMS), immunoaffinity mass spectrometry, surface enhanced laser desorption/ionization in time of flight mass spectrometry (SELDI-TOF-MS), matrix assisted laser desorption/ionization mass spectrometry (MALDI) or other antibody chip techniques.

The invention is not limited by the types of methods used to determine the quantities of autoantibodies.

Using the methods of the invention an individual is classified as a VEGF antagonist responder if the amounts of one or several of Group A autoantibodies selected from antibodies directed against MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1, SELO, SOD, ENO2 are increased or decreased by at least 10%, by 20%, by 30%, by 40%, by 50%, by 100%, by 150%, by 200%, by 250%, preferably by 25%-150%, more preferably by 50-100%, in the sample compared to a control (healthy individual).

Using the methods of the invention an individual having dry AMD is classified as having a risk that the dry AMD converts into wet AMD if the amounts of one or several autoantibodies selected from antibodies of Group A antibodies comprising antibodies directed against: MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1, SELO, SOD, ENO2 or if the amounts of one or several autoantibodies selected from antibodies of Group B antibodies comprising antibodies directed against: alpha-synuclein, SELO, SPRY, GAPDH-H2, Annexin-V, THAP, VTI-B, HSP10, ESD, PKC80, ACO2-C2, OGFR, PBP-I2, CAZ-C3, EIFA1, MAPK3, ENO1-H7, Chromosome17, Aconitate Hydratase, GPX4 detected and quantified in two samples taken in a time period of about 2 weeks, of about 1 month, of about 2 months, of about 6 months, of about 12 months, of at least about 12 months, decrease by at least 20%, by 30%, by 40%, by 50%, by 60%, by 75%, preferably by at least 30%, more preferably by at least 50%, in the sample compared to a control (healthy individual).

The methods described herein can be utilized as a diagnostic assay to identify those subjects having wet AMD who are likely to respond to a VEGF antagonist. The methods of the invention can be used to determine whether a subject should be administered a VEGF antagonist to reduce the severity of wet AMD. The methods described herein can also be utilized as a prognostic assay to identify those subjects having dry AMD who are at risk to develop wet AMD and who would benefit from receiving a VEGF antagonist. Prognostic assays can be used for predictive purposes or prophylactic purposes to treat an individual who is at risk to develop wet AMD.

The invention also encompasses kits for determining the level of one or several autoantibodies directed against MAPK3, OGFR, PolyRp2, Chromosome 17, EIFA1, GPX4, SRP14, Gamma-synuclein, Jo-1, Pre-Albumin, GPD2, AP1M1, ENO1-H7, PRG2, ATP synthase, GNB1-A3, TUBB3, HSP 60, ICA1 and SELO, SOD, ENO2.

MODES FOR CARRYING OUT THE INVENTION

I. Comparison of Immunoreactivities in Dry and Wet AMD

The autoantibody patterns against retinal antigens in sera of patients with "wet" AMD were analyzed and compared to healthy control subjects and patients with "dry" AMD by mass spectrometry (MS) approach. It is known that two third of serum immunoglobulins in healthy individuals are natural occurring autoantibodies, so that complex profiles exist even in healthy people and disease specific changes of circulating autoantibodies are known from several other diseases, e.g. glaucoma or Sicca syndrome. After successful de novo screening of immunoreactivities using MS-based approach and high density Protagen antigen microarrays, a customized antigen microarray containing 61 antigens was built (Table 2). Each microarray contained each antigen as triplicate. Patients were included in the study based on the protocol following all inclusion- and exclusion criteria.

TABLE 1

Breakdown Table of Descriptive Statistics.

| Group | Gender (m/f) | Age - Means | Number of subjects | Age - Std. Dev. |
|---|---|---|---|---|
| CTRL | f | 71.8 | 9 | 9.4 |
| CTRL | m | 74.5 | 11 | 11.0 |
| 17 | f | 80.9 | 14 | 8.5 |

TABLE 1-continued

Breakdown Table of Descriptive Statistics.

| Group | Gender (m/f) | Age - Means | Number of subjects | Age - Std. Dev. |
|---|---|---|---|---|
| 17 | m | 73.2 | 6 | 7.2 |
| 18 | f | 81.0 | 120 | 7.9 |
| 18 | m | 81.4 | 60 | 5.1 |
| 19 | f | 82.8 | 64 | 6.9 |
| 19 | m | 78.4 | 45 | 5.1 |
| All Groups | | 80.4 | 329 | 7.5 |

CTRL = healthy volunteers,
17 = dry AMD,
18 = wet AMD starting new anti-VEGF treatment,
19 = wet AMD continuous anti-VEGF treatment Analysis of immunoreactivities of IgG against these 61 antigens was performed in 329 samples. For all samples, complex patterns of immunoreactivities could be found.

TABLE 2

List of antigens on customized microarray:

| UniProt ID | MW kDa | Protein name UniProt | Protein name | Abbreviation in Study |
|---|---|---|---|---|
| P62937 | 18.0 | Peptidyl-prolyl cis-trans isomerase A (Cyclophilin A) | Cyclophilin A human | Cyclophilin B |
| P61604 | 10.9 | 10 kDa heat shock protein, mitochondrial (Hsp10) | Chaperonin 10, Recombinant, Human | HSP 10 |
| P00441 | 15.9 | Superoxide dismutase [Cu—Zn] | Superoxide Dismutase from bovine erythrocytes | SOD |
| P02686 | 33.1 | Myelin basic protein (MBP); Isoform 1 | Myelin Basic Protein from bovine brain | MBP |
| P04792 | 22.8 | Heat shock protein beta-1 (Heat shock 27 kDa protein; Hsp27) | Hsp27 Protein - Low Endotoxin | HSP 27 |
| P08107 | 70.1 | Heat shock 70 kDa protein 1A/1B (Hsp70.1/Hsp70.2) | Heat Shock Protein 70 from bovine brain | HSP 70 |
| P02751 | 262.6 | Fibronectin; Isoform 1 | Fibronectin from human plasma | Fibronektin |
| P01009 | 46.7 | Alpha-1-antitrypsin | α1-Antitrypsin from human plasma | Alpha-1-Antitrypsin |
| P08758 | 35.9 | Annexin A5 | Annexin V from human placenta | Annexin V |
| Q14694 | 87.1 | Ubiquitin carboxyl-terminal hydrolase 10 (USP10) | Ubiquitin human | Ubiquitin |
| P49773 | 13.8 | Histidine triad nucleotide-binding protein 1 (Protein kinase C inhibitor 1) | Protein Kinase C Inhibitor, Myristoylated | PKC Inhibitor |
| P02766 | 15.9 | Transthyretin (Prealbumin) | Prealbumin from human plasma | PreAlbumin |
| O76070 | 13.3 | Gamma-synuclein | γ-Synuclein human | Gamma-synuclein |
| P14136 | 49.9 | Glial fibrillary acidic protein (GFAP) | Anti-Glial Fibrillary Acidic Protein | GFAP |
| P27797 | 48.1 | Calreticulin | Calreticulin from bovine liver | Calretikulin |
| P02549 | 280.0 | Spectrin alpha chain, erythrocyte | Spectrin from human erythrocytes | Spektrin |
| P12081 | 57.4 | Histidine-tRNA ligase, cytoplasmic (JO-1) | JO-1 human | Jo-1 |
| P10809 | 61.1 | 60 kDa heat shock protein mitochondrial (Hsp60) | HSP60 (human), (recombinant) | HSP 60 |
| P53674 | 28.0 | Beta-crystallin B1 | βL-Crystallin from bovine eye lens | Beta-L-Chrystalin |
| P09211 | 23.4 | Glutathione S-transferase P | Glutathione S-Transferase from bovine liver | GST |
| P68133 | 42.1 | Actin, alpha skeletal muscle | Actin from bovine muscle | Actin |

TABLE 2-continued

List of antigens on customized microarray:

| UniProt ID | MW kDa | Protein name UniProt | Protein name | Abbreviation in Study |
|---|---|---|---|---|
| P15104 | 42.1 | Glutamine synthetase | Glutamine synthetase | GLUL |
| Q99798 | 83.4 | Aconitase 2, mitochondrial | aconitase 2, mitochondrial | ACO2 |
| E5RFU4 | 18.3 | Dihydropyrimidinase-like 2 | Dihydropyrimidinase-like 2 | DBYSL2 |
| P09936 | 24.8 | Ubiquitin carboxyl-terminal hydrolase isozyme L1 (UCHL1) | Ubiquitin carboxyl-terminal hydrolase isozyme L1 | VCHC1 |
| P30086 | 21.1 | Phosphatidylethanolamine-binding protein 1 | Phosphatidylethanolamine-binding protein 1 | PBP |
| P00918 | 29.2 | Carbonic anhydrase 2 | Carbonic Anhydrase II | CAZ |
| P12277 | 42.6 | Creatine kinase B-type | Creatine kinase B | CKB |
| P62873 | 37.4 | Guanine nucleotide-binding protein G(I)/G(S)/G(T) subunit beta-1 (GNB1) | Guanine nucleotide-binding protein G(1)/G(S)/G(T) subunit beta 1 | GNB1 |
| P06733 | 47.2 | Alpha-enolase | Alpha-Enolase | ENO1 |
| P04406 | 36.1 | Glyceraldehyde-3-phosphate dehydrogenase (GAPDH) | Glyceraldeyde (3-)phosphate dehydrogenase | GAPDH |
| P60842 | 46.2 | Eukaryotic initiation factor 4A-I | *Homo sapiens* eukaryotic translation initiation factor 4A isoform 1 (EIF4A1) mRNA | EIFA1 |
| A8K318 | 59.2 | Protein kinase C substrate 80K-H | protein kinase C substrate 80K-H isoform 2 [*Homo sapiens*] | PKC80 |
| Q68Y55 | 34.9 | Poly(RC) binding protein 2 | poly(rC) binding protein 2 isoform g [*Homo sapiens*] | PolyRp2 |
| P49761 | 58.6 | CDC-like kinase 3 (CLK3), transcript variant phclk3, mRNA | *Homo sapiens* CDC-like kinase 3 (CLK3); transcript variant phclk3; mRNA | CLK3 |
| Q9P2Z0 | 28.4 | THAP domain-containing protein 10 | THAP domain containing 10 [*Homo sapiens*] | THAP |
| Q9BXS5 | 48.6 | AP-1 complex subunit mu-1 (AP1M1) | *Homo sapiens* adaptor-related protein complex 1; mu 1 subunit (AP1M1); mRNA | AP1M1 |
| P63330 | 35.6 | Serine/threonine-protein phosphatase 2A catalytic subunit alpha isoform | protein phosphatase type 2A catalytic subunit alpha isoform [*Mus musculus*] | pp2A |
| Q9NZT2 | 73.3 | Opioid growth factor receptor | *Homo sapiens* opioid growth factor receptor (OGFR). mRNA | OGFR |
|  |  |  | *Homo sapiens* plasticity-related gene 2 (PRG2) mRNA | PRG2 |
| P43235 | 37.0 | Cathepsin K | cathepsin K preproprotein [*Homo sapiens*] | Catepsin |
| Q53G92 | 50.4 | Tubulin beta-3 chain | *Homo sapiens* tubulin beta 3 (TUBB3) mRNA | TUBB3 |
| P37108 | 14.6 | Signal recognition particle 14 kDa protein | *Homo sapiens* signal recognition particle 14 kDa (homologous Alu RNA binding protein) (SRP14) mRNA | SRP14 |
| Q7Z6Z7 | 481.9 | E3 ubiquitin-protein ligase HUWE1; Isoform 1 | HUWE1 protein [*Homo sapiens*] | HUWE1 |
|  |  |  | *Homo sapiens* chromosome X genomic contig. reference assembly | ChromosomX |
| Q96S16 | 36.9 | JmjC domain-containing protein 8 (Jumonji domain-containing protein 8) | jumonji domain containing 8 [*Homo sapiens*] | jumonji |
| Q96N21 | 55.1 | Uncharacterized protein C17orf56 | *Homo sapiens* chromosome 17 open reading frame 56 (C17orf56). mRNA | Chromosome 17 |
| Q96HG3 | 54.6 | Islet cell autoantigen 1, 69 kDa | *Homo sapiens* islet cell autoantigen 1. 69 kDa (ICA1). transcript variant 2. mRNA | ICA1 |

TABLE 2-continued

List of antigens on customized microarray:

| UniProt ID | MW kDa | Protein name UniProt | Protein name | Abbreviation in Study |
|---|---|---|---|---|
| P10768 | 31.5 | S-formylglutathione hydrolase (Esterase D) | *Homo sapiens* esterase D/formylglutathione hydrolase (ESD) | ESD |
| P25325 | 33.2 | 3-mercaptopyruvate sulfurtransferase | mercaptopyruvate sulfurtransferase isoform 2 [*Homo sapiens*] | MSI 2 |
| P27361 | 43.1 | Mitogen-activated protein kinase 3; Isoform 1 | *Homo sapiens* mitogen-activated protein kinase 3 (MAPK3); transcript variant 1; mRNA | MAPK3 |
| P43304 | 80.9 | Glycerol-3-phosphate dehydrogenase, mitochondrial (GPD2); Isoform 1 | *Homo sapiens* glycerol-3-phosphate dehydrogenase 2 (mitochondrial) (GPD2); mRNA | GPD2 |
| P36969 | 22.2 | Phospholipid hydroperoxide glutathione peroxidase, mitochondrial | *Homo sapiens* glutathione peroxidase 4 (phospholipid hydroperoxidase) (GPX4).transcript variant 1. mRNA | GPX4 |
| B7Z4U7 | 65.1 | Sec1 family domain containing 1, isoform CRA_b | vesicle transport-related protein isoform b [*Homo sapiens*] | VTI-B |
| Q9BVL4 | 73.5 | Selenoprotein O | *Homo sapiens* selenoprotein O (SELO) mRNA | SELO |
| Q6PJ21 | 39.4 | SPRY domain-containing SOCS box protein 3 | SPRY domain-containing SOCS box protein SSB-3 | SPRX |
| P35611 | 81.0 | Alpha-adducin | adducin 1 (alpha) isoform c [*Homo sapiens*] | Adduccin |
| Q99798 | 85.4 | Aconitate hydratase, mitochondrial | Aconitate Hydratase 2 (mitochondrial) | Aconitate Hydratase |
| P06576 | 56.6 | ATP synthase subunit beta, mitochondrial | ATP synthase | ATP Synthase |
| P40926 | 35.5 | Malate dehydrogenase, mitochondrial | Malat dehydrogenase | Malat De-hydrogenase |
| P37840 | 14.5 | Alpha-synuclein | alpha-synuclein | Alpha Synuclein |
| P10636 | 78.9 | Microtubule-associated protein tau | tau | TAU |
| P05067 | 86.9 | Amyloid beta A4 protein (Alzheimer disease amyloid protein) | beta-amyloid | Beta-Amyloid |
| Q05923 | 34.4 | Dual specificity protein phosphatase 2 | DUSP2 dual specificity phosphatase 2 [*Homo sapiens*] | DUSP2 |
| Q14166 | 74.4 | Tubulin-tyrosine ligase-like protein 12 | *Homo sapiens* tubulin tyrosine ligase-like family member 12 (TTLL12) mRNA | TTLL2 |
| P09104 | 47.3 | Gamma-enolase | Gamma-enolase | ENO2 |
| P00441 | 15.9 | Superoxide dismutase | Superoxide dismutase [Cu—Zn] | SOD |

The immunoreactivities were analyzed in patients suffering from dry AMD, wet AMD, and compared to healthy controls. Table 3 shows the results of ANOVA analysis and their corresponding p-values for the most-significant antigens.

The immunoreactivities of dry and wet AMD patients are highly significantly different from each other and from controls. Although as part of natural autoimmunity also in healthy subjects complex antibody patterns against the tested antigens could be shown, the patterns in both AMD groups are changed. One of the most prominently changed reactivity is against alpha-synuclein. Alpha-synuclein is known from other neurodegenerative diseases. Others are heat shock proteins (e.g. HSP 10) and also Annexin V, which plays a major role in apoptotic processes. Some others are antithetic regulated in wet and dry-AMD such as VTI-B, PBP-12, and OGFR. Pathway comparison analysis revealed protein functions particularly found in immunological diseases, especially aconitase 2, which plays a role in citric acid cycle, further enolase 1, Annexin V, mitogen-activated protein kinase C (MAPK3) and Alpha-Synuclein. Mutations in Alpha-synuclein e.g. are associated with Parkinson's disease, Alzheimer's disease, and several other neurodegenerative illnesses. Annexin 5 is a phospholipase A2 and protein kinase C inhibitory protein with calcium channel activity and a potential role in cellular signal transduction, inflammation, growth and differentiation. Apart from the immunological markers, bio functions playing a major role in inflammation could be observed, like e.g. Alpha-synuclein, aconitase 2, enolase 1 and GADPH (glyceraldehyde-phosphate dehydrogenase), which acts in apoptotic processes and is also known to play a role in Alzheimer's disease. Annexin V is proposed to have anti-apoptotic and anti-inflammatory functions, comparison of immunoreactivities in our study revealed higher reactivity in the dry AMD-group. It could clearly be demonstrated that there are huge differences in the immunoreactivities in both wet and dry AMD groups.

TABLE 3

ANOVA (Analysis of Variance) of the IgG immunoreactivities in patients with wet AMD, dry AMD, and compared to controls. The table reveals the most significant antigens and according p-values.

| | CTRL-AV | CTRL-SE | AMDDRY-AV | AMDDRY-SE | AMDWET-AV | AMDWET-SE | ANOVA-P |
|---|---|---|---|---|---|---|---|
| Alpha Synuclein | 6428 | 487 | 10667 | 1974 | 7221 | 251 | 0.003 |
| SELO | 31155 | 1755 | 27412 | 1733 | 26330 | 397 | 0.01 |
| SPRY | 24905 | 1445 | 21287 | 808 | 22305 | 265 | 0.028 |
| GAPDH - H2 | 11571 | 821 | 13277 | 1137 | 14926 | 360 | 0.031 |
| Annexin V | 14977 | 1821 | 18675 | 1422 | 15258 | 321 | 0.034 |
| THAP | 14422 | 1575 | 10767 | 715 | 11889 | 284 | 0.044 |
| VTI-B | 22121 | 1816 | 19333 | 1493 | 23773 | 512 | 0.065 |
| HSP 10 | 16099 | 1313 | 20613 | 1716 | 19235 | 385 | 0.071 |
| ESD | 29416 | 1393 | 24942 | 995 | 26008 | 424 | 0.082 |
| PKC80 | 23592 | 1798 | 21236 | 1396 | 20575 | 335 | 0.082 |
| ACO2 - C2 | 19238 | 1478 | 17569 | 1462 | 16185 | 376 | 0.089 |
| OGFR | 18774 | 2383 | 21865 | 3017 | 17521 | 516 | 0.115 |
| PBP - I2 | 21243 | 1455 | 24279 | 1422 | 24944 | 467 | 0.119 |
| CAZ - C3 | 5373 | 595 | 7534 | 1274 | 6402 | 196 | 0.148 |
| EIFA1 | 26612 | 2773 | 21695 | 2045 | 21915 | 612 | 0.15 |
| MAPK3 | 28505 | 1571 | 25186 | 1110 | 27123 | 315 | 0.15 |
| ENO1 - H7 | 19297 | 1419 | 25493 | 2798 | 22685 | 594 | 0.15 |
| Chromosome 17 | 20439 | 1587 | 18881 | 1513 | 21993 | 455 | 0.16 |
| Aconitate Hydratase | 20584 | 1720 | 18805 | 1622 | 17738 | 391 | 0.163 |
| GPX4 | 19207 | 1159 | 17929 | 1277 | 17190 | 283 | 0.177 |

(AV = average; SE = standard error; p = p-value)

II. Longitudinal Analysis of IgG Immunoreactivities in Wet AMD

To answer the question if the injection of Lucentis which is basically a foreign protein to the body, is able to provoke a significant immune reaction, a longitudinal analysis of IgG immunoreactivities was performed. FIG. 1 shows the IgG pattern analysis in wet AMD patients. The samples were taken before, and 2, 3, 4, 6, and 12 months after starting lucentis treatment. Table 4 reveals the most significant antibody reactivities changing after starting treatment with lucentis. Overall, no clear increase in immunoreactivities could be observed after the lucentis treatment. Most significant change is shown for MAPK3. No single antigen revealed significant changes in univariate ANOVA. However, the Mahalanobis distances could reveal several significant differences in multivariate analysis taken the complete antibody/antigen pattern simultaneously, especially between the later time points. Furthermore, no differentiation between the groups could be detected in multivariate canonical root analysis.

TABLE 4

Longitudinal analysis over 12 months of IgG immunoreactivities in wet AMD patients, who started with lucentis treatment. Wilks' Lamda: values in the range of 0 (perfect discrimination) to 1 (no discrimination), Partial Lambda: The Wilks' Lambda associated with the unique contribution of the respective variable to the discriminatory power of the model.

| | Wilks'-Lambda | Partial-Lambda | p-value |
|---|---|---|---|
| TAU-n | 0.793690 | 0.946549 | 0.143135 |
| ACO2-C2-n | 0.802293 | 0.936398 | 0.084057 |
| MAPK3-n | 0.810685 | 0.926705 | 0.049457 |
| ATP synthase-n | 0.788763 | 0.952462 | 0.192688 |
| GPD2-n | 0.784479 | 0.957663 | 0.248013 |
| AP1M1-n | 0.777703 | 0.966006 | 0.364065 |

Figure 4:
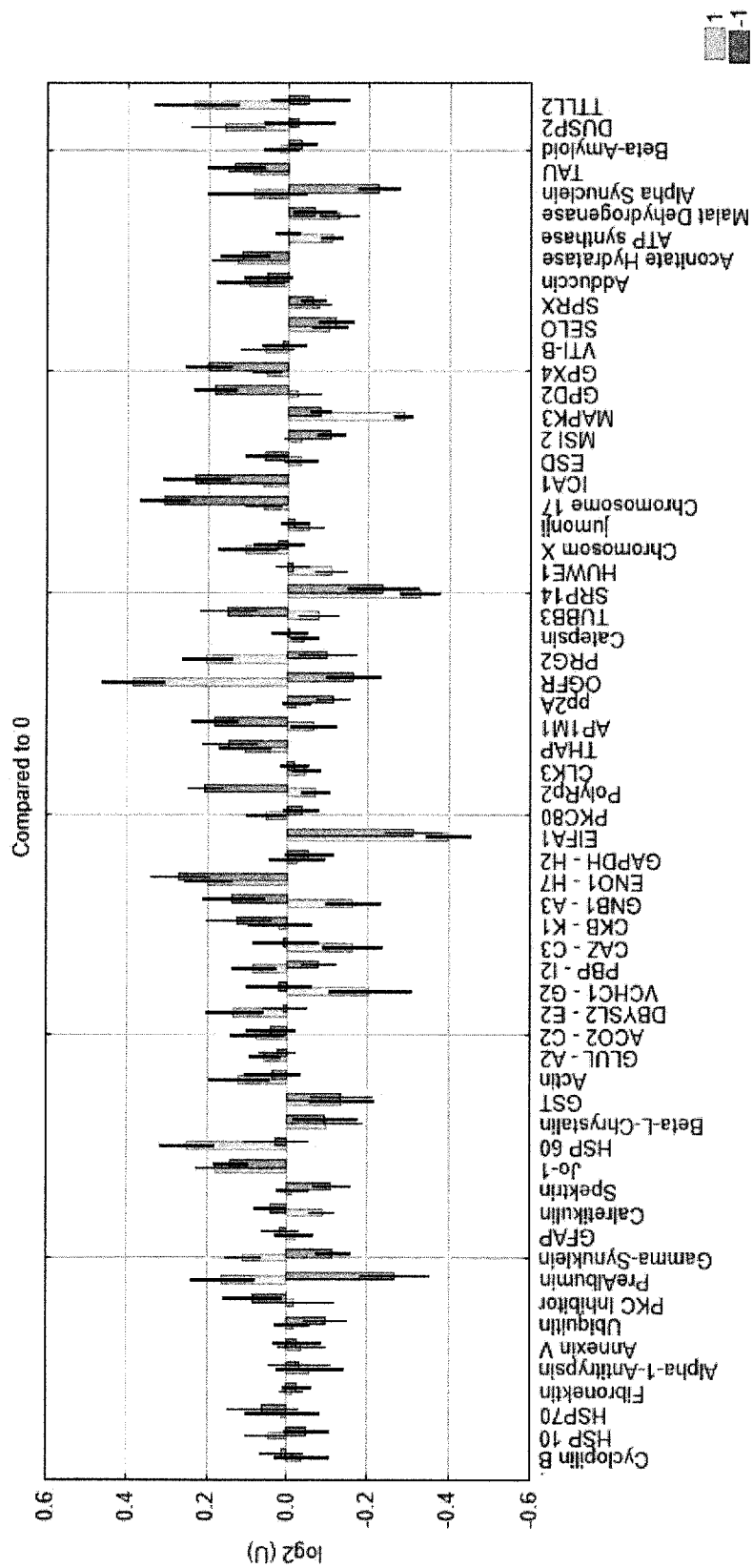
FIG. 4: Comparison of immunoreactivities in patients suffering from wet AMD. The patients were divided into those showing vision loss (−1), no change in vision (0), or improvement of vision (1). All immunoreactivities.
Figure 5:
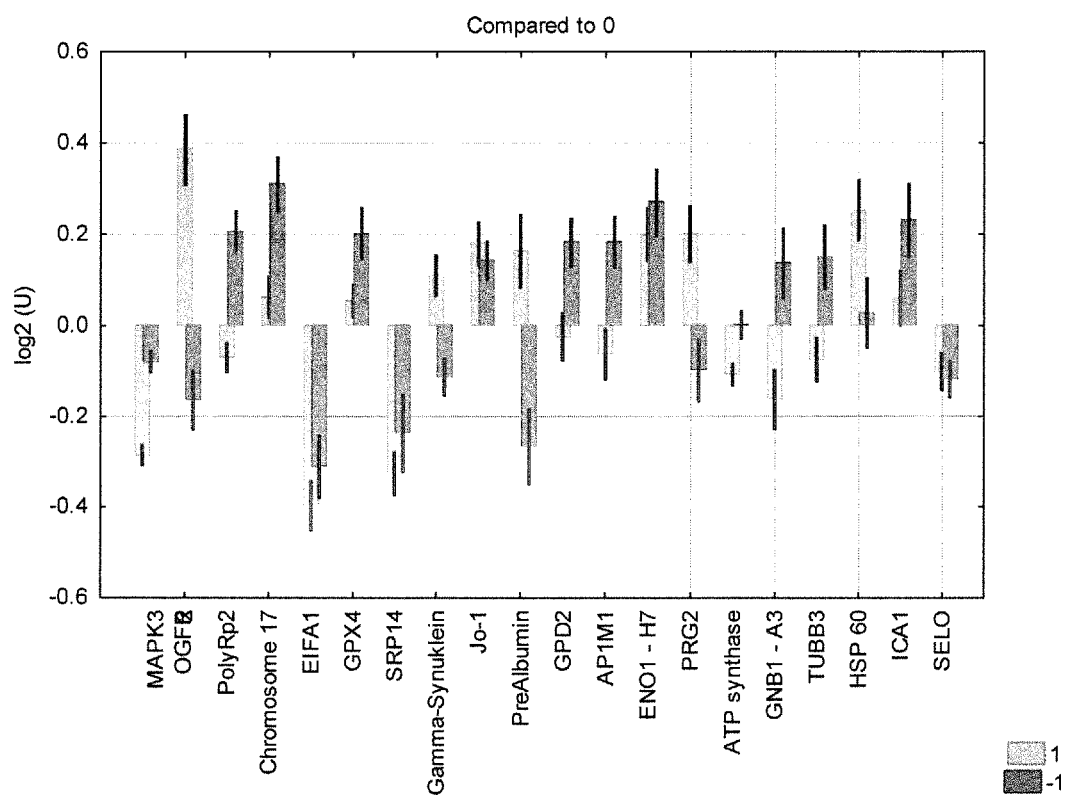
FIG. 5: Comparison of immunoreactivities in patients suffering from wet AMD. The patients were divided into those showing vision loss (−1), no change in vision (0), or improvement of vision (1). 20 most significant reactivities.
Figure 6:
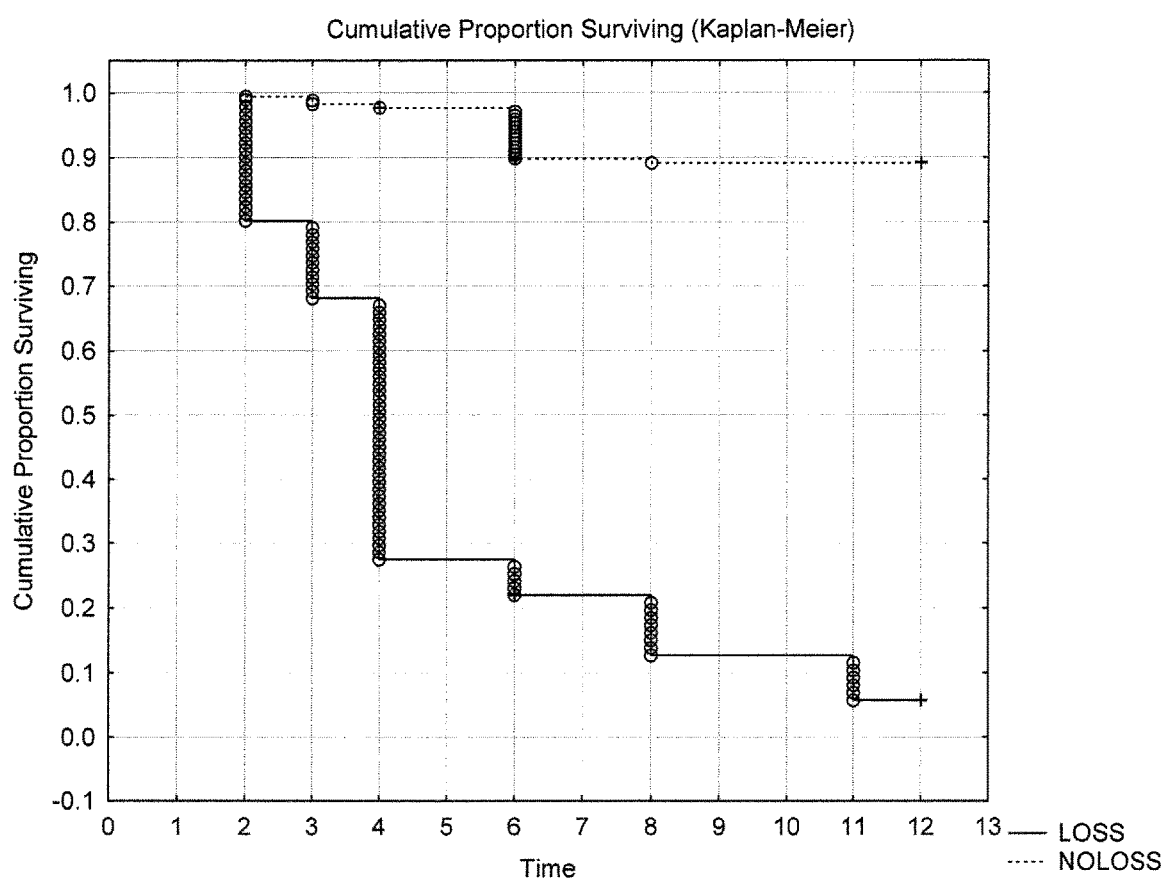
FIG. 6: The results of the data mining procedures (C&RT and artificial neural networks) were used as input for this analysis. A survival analysis (Kaplan-Meier analysis, Cumulative proportion surviving) was performed to assess how strongly the classification of the data mining procedures influence the survival time (time to vision loss) in this 12 months study.

III. Analysis of IgG Immunoreactivities in Wet AMD: Influence of Success of Treatment The immunoreactivities in patients suffering from wet AMD depending on success of treatment were compared. Based on visual acuity (log mar) the patients were divided into those showing vision loss during the 12 months treatment by lucentis (−1), no change in vision (0), or improvement of vision (1). Highly significant changes could be observed between those immunoreactivities from patients showing an improvement of vision during lucentis treatment and those who do not. FIG. 4 and FIG. 5 compare the IgG reactivities and reveal the most significant changes. Furthermore, ANOVA could demonstrate highly significant changes in a large number of antigens (Table 5 and Table 6). Multivariate canonical root analysis could reveal a good differentiation between the groups.

TABLE 5

ANOVA of immunoreactivities in wet AMD patients depending on treatment.
The patients were divided into those showing vision loss (−1),
no change in vision (0), or improvement of vision (1).

|  | 0-AV | 0- SE | 1-AV | 1- SE | −1-AV | −1- SE | ANOVA - P |
|---|---|---|---|---|---|---|---|
| Cyclopilin B | 33179 | 949 | 32345 | 1463 | 33452 | 1221 | 0.813 |
| HSP 10 | 19235 | 579 | 19821 | 837 | 18591 | 704 | 0.496 |
| HSP70 | 7866 | 341 | 7942 | 501 | 8207 | 492 | 0.837 |
| Fibronektin | 27083 | 472 | 26845 | 512 | 26608 | 656 | 0.816 |
| Alpha-1-Anti-trypsin | 13139 | 552 | 12626 | 725 | 12866 | 675 | 0.853 |
| Annexin V | 15507 | 487 | 15107 | 620 | 15243 | 633 | 0.879 |
| Ubiquitin | 17679 | 597 | 17507 | 504 | 16529 | 616 | 0.332 |
| PKC Inhibitor | 12519 | 587 | 12385 | 857 | 13294 | 669 | 0.615 |
| PreAlbumin | 15562 | 873 | 17430 | 962 | 12944 | 756 | 0.003 |
| Gamma-synuclein | 22228 | 618 | 23983 | 746 | 20546 | 600 | 0.003 |
| GFAP | 35195 | 783 | 34749 | 1139 | 35638 | 1126 | 0.839 |
| Calretikulin | 32672 | 877 | 30756 | 640 | 33606 | 945 | 0.094 |
| Spektrin | 24946 | 619 | 24708 | 670 | 23095 | 730 | 0.107 |
| Jo-1 | 27542 | 590 | 31206 | 1049 | 30400 | 892 | 0.003 |
| HSP 60 | 23144 | 988 | 27559 | 1267 | 23609 | 1274 | 0.022 |
| Beta-L-Chrystalin | 11728 | 478 | 10959 | 666 | 11006 | 605 | 0.538 |
| GST | 16706 | 684 | 15214 | 830 | 15230 | 811 | 0.259 |
| Actin | 23996 | 958 | 26141 | 1356 | 24624 | 1187 | 0.421 |
| GLUL - A2 | 19825 | 607 | 20624 | 546 | 20164 | 614 | 0.66 |
| ACO2 - C2 | 15714 | 601 | 16579 | 781 | 16185 | 675 | 0.665 |
| DBYSL2 - E2 | 19515 | 748 | 21426 | 1050 | 19609 | 732 | 0.228 |
| VCHC1 - G2 | 11973 | 608 | 10395 | 722 | 12151 | 678 | 0.164 |
| PBP - I2 | 24591 | 697 | 26074 | 1009 | 23293 | 718 | 0.069 |
| CAZ - C3 | 6615 | 341 | 5919 | 300 | 6646 | 378 | 0.306 |
| CKB - K1 | 4835 | 167 | 4906 | 267 | 5269 | 294 | 0.375 |
| GNB1 - A3 | 7772 | 329 | 6949 | 320 | 8550 | 456 | 0.021 |
| ENO1 - H7 | 19856 | 753 | 22785 | 935 | 23954 | 1210 | 0.005 |
| GAPDH - H2 | 15272 | 614 | 15041 | 719 | 14734 | 597 | 0.826 |
| EIFA1 | 25391 | 1158 | 19280 | 745 | 20476 | 1000 | 0 |
| PKC80 | 20766 | 484 | 21545 | 741 | 20276 | 588 | 0.359 |
| PolyRp2 | 15683 | 385 | 14937 | 350 | 18082 | 549 | 0 |
| CLK3 | 28064 | 571 | 27181 | 646 | 27717 | 639 | 0.612 |
| THAP | 11395 | 386 | 12273 | 567 | 12608 | 586 | 0.178 |
| AP1M1 | 10985 | 346 | 10519 | 408 | 12470 | 482 | 0.004 |
| pp2A | 24322 | 591 | 23963 | 598 | 22493 | 655 | 0.085 |
| OGFR | 16924 | 804 | 22120 | 1178 | 15111 | 691 | 0 |
| PRG2 | 26929 | 1146 | 30959 | 1337 | 25169 | 1230 | 0.008 |
| Catepsin | 24577 | 707 | 23876 | 584 | 24513 | 778 | 0.774 |
| TUBB3 | 12899 | 382 | 12244 | 415 | 14315 | 693 | 0.021 |
| SRP14 | 25498 | 1073 | 20329 | 692 | 21662 | 1301 | 0.002 |
| HUWE1 | 25755 | 585 | 23901 | 645 | 25528 | 716 | 0.119 |
| Chromosom X | 11364 | 483 | 12210 | 612 | 11548 | 497 | 0.522 |
| jumonji | 18742 | 344 | 18098 | 491 | 18518 | 442 | 0.559 |
| Chromosome 17 | 20052 | 584 | 20932 | 667 | 24848 | 1044 | 0 |
| ICA1 | 16622 | 618 | 17327 | 725 | 19514 | 1099 | 0.033 |
| ESD | 25863 | 580 | 25324 | 700 | 26872 | 978 | 0.38 |
| MSI 2 | 26033 | 684 | 25447 | 733 | 24186 | 586 | 0.13 |
| MAPK3 | 28919 | 577 | 23712 | 375 | 27368 | 470 | 0 |
| GPD2 | 20415 | 526 | 20057 | 731 | 23181 | 852 | 0.003 |
| GPX4 | 16304 | 277 | 16926 | 435 | 18737 | 728 | 0.001 |
| VTI-B | 23423 | 828 | 24339 | 1089 | 23596 | 882 | 0.777 |
| SELO | 27500 | 632 | 25618 | 749 | 25330 | 735 | 0.046 |
| SPRX | 22907 | 463 | 21735 | 452 | 21944 | 457 | 0.15 |
| Adduccin | 12874 | 419 | 13792 | 797 | 13348 | 558 | 0.522 |
| Aconitate Hydratase | 16576 | 509 | 18093 | 817 | 17913 | 746 | 0.193 |
| ATP synthase | 27814 | 440 | 25813 | 469 | 27848 | 601 | 0.011 |
| Malat Dehydrogenase | 27349 | 844 | 25088 | 847 | 26175 | 984 | 0.216 |
| Alpha Synuclein | 7553 | 398 | 8008 | 694 | 6464 | 231 | 0.056 |
| TAU | 12493 | 374 | 13288 | 576 | 13714 | 663 | 0.219 |
| Beta-Amyloid | 8235 | 161 | 8344 | 246 | 8042 | 198 | 0.576 |
| DUSP2 | 12211 | 725 | 13610 | 856 | 12014 | 721 | 0.33 |
| TTLL2 | 16754 | 1387 | 19730 | 1426 | 16204 | 1103 | 0.18 |
| SOD | 1361 | 728 | 287 | 892 | 1460 | 659 |  |
| ENO2 | 9538 | 13415 | 9267 | 16430 | 27101 | 12134 |  |

(AV = average, SE = standard error, p = p-value)

TABLE 6

ANOVA of immunoreactivities in wet AMD patients depending on treatment. The patients were divided into those showing vision loss (−1), no change in vision (0), or improvement of vision (1).

| | 0-AV | 0- SE | 1-AV | 1- SE | −1-AV | −1-SE | ANOVA - P |
|---|---|---|---|---|---|---|---|
| MAPK3 | 28919 | 577 | 23712 | 375 | 27368 | 470 | 0 |
| OGFR | 16924 | 804 | 22120 | 1178 | 15111 | 691 | 0 |
| PolyRp2 | 15683 | 385 | 14937 | 350 | 18082 | 549 | 0 |
| Chromosome 17 | 20052 | 584 | 20932 | 667 | 24848 | 1044 | 0 |
| EIFA1 | 25391 | 1158 | 19280 | 745 | 20476 | 1000 | 0 |
| GPX4 | 16304 | 277 | 16926 | 435 | 18737 | 728 | 0.001 |
| SRP14 | 25498 | 1073 | 20329 | 692 | 21662 | 1301 | 0.002 |
| Gamma-synuclein | 22228 | 618 | 23983 | 746 | 20546 | 600 | 0.003 |
| Jo-1 | 27542 | 590 | 31206 | 1049 | 30400 | 892 | 0.003 |
| PreAlbumin | 15562 | 873 | 17430 | 962 | 12944 | 756 | 0.003 |
| GPD2 | 20415 | 526 | 20057 | 731 | 23181 | 852 | 0.003 |
| AP1M1 | 10985 | 346 | 10519 | 408 | 12470 | 482 | 0.004 |
| ENO1 - H7 | 19856 | 753 | 22785 | 935 | 23954 | 1210 | 0.005 |
| PRG2 | 26929 | 1146 | 30959 | 1337 | 25169 | 1230 | 0.008 |
| ATP synthase | 27814 | 440 | 25813 | 469 | 27848 | 601 | 0.011 |
| GNB1 - A3 | 7772 | 329 | 6949 | 320 | 8550 | 456 | 0.021 |
| TUBB3 | 12899 | 382 | 12244 | 415 | 14315 | 693 | 0.021 |
| HSP 60 | 23144 | 988 | 27559 | 1267 | 23609 | 1274 | 0.022 |
| ICA1 | 16622 | 618 | 17327 | 725 | 19514 | 1099 | 0.033 |
| SELO | 27500 | 632 | 25618 | 749 | 25330 | 735 | 0.046 |

(AV = average, SE = standard error, p = p-value)

Additionally, a general regression model (GRM) was performed to analyze if there is a longitudinal effect on the antibody patterns depending on success of treatment. Several antigens could be detected which show significant longitudinal effects.

Thus, the immunoreactivities could have predictive value to determine the treatment effect of lucentis in AMD patients. Involved are antigens such as MAPK3, Gamma-synuclein, different heat shock proteins and many others. Several of the immunoreactivities are regulated in opposed directions. E.g. immunoreactivities against OGFR, Gamma-synuclein, pre-albumin, and PRG2 are up-regulated in patients improving vision during 12 months under lucentis therapy and down-regulated in those who do not. Furthermore, e.g. immunoreactivities against PolyRp2, GNB1-A3, and TUBB3 are down-regulated in patients improving vision during 12 months under lucentis treatment and up-regulated in those who do not. Furthermore, e.g. some heat shock proteins show huge difference in IgG immunoreactivities against them.

Pathway analysis showed that nine proteins were associated with cellular growth and proliferation, namely ATP synthase, eukaryotic translation initiation factor 4A1 (EIFA1), enolase 1, glutathione peroxidase 4 (GPX4), HSP60, MAPK3, Opioid growth factor receptor (OGFR), Gamma-Synuclein and beta Tubulin (TUBB3). Immunoreactivities against OGFR were up-regulated in patients improving in vision under lucentis therapy, whereas a down-regulation was observed in case of vision loss.

IV. Predictive Value of Immunoreactivities on Success of Treatment

Based on visual acuity (log mar) the patients were divided into those showing vision loss during the 12 months treatment by lucentis (−1), no change in vision (0), or improvement of vision (1). Highly significant changes could be observed between those immunoreactivities from patients showing an improvement of vision during lucentis treatment and those who do not. If the immunoreactivities might have predictive value on lucentis treatment, data mining models could be useful to distinguish between those patients just based on their antibody patterns.

C&RT models (general classification/regression tree models) were performed. Furthermore, an artificial neural network was trained to recognize those antibody patterns which are correlated with a successful treatment with lucentis. After training, those patterns could be recognized with a sensitivity and specificity of about 95%. Nevertheless, it is important to consider that the number of patients in this pilot study is small and further validation studies in larger cohorts are needed to address the predictive value in detail. The most discrimination power was attributed to e.g. OGFR, SPR14, pre-albumin etc. which also were important immunoreactivities in the preceding analyses.

V. Predictive Value of Immunoreactivities on Course of Vision Loss

The results of the data mining procedures (C&RT and artificial neural networks) were used as input for this analysis. A survival analysis (Kaplan-Meier analysis, Cumulative proportion surviving) was performed to assess how strongly the classification of the data mining procedures influence the survival time (time to vision loss) in this 12 months study.

The Kaplan-Meier plot demonstrates the huge impact this a priori classification based on their antibody patterns has on the outcome of lucentis treatment over time.

Whereas those patients classified as good lucentis responder show nearly no vision loss in survival analysis, the other group (bad lucentis responder) reveal strong vision loss.

VI. Influence of Other Clinical Parameter on Immunoreactivities

A component of variance analysis was performed to assess the effect of the parameters vision change, retinal hemorrhage, macular edema, and choroidal neovascularization (CNV) on immunoreactivities. There are no very clear singular effects of these clinical parameters on the immunoreactivity levels for each antigen. For all of the antigens, the effect of change in vision, retinal hemorrhage, macular edema, or CNV are very small and not significant. However, the interaction between those (e.g. 1*2*3*4) can have a larger impact on the antibody patterns.

Mass Spectrometric Analysis

The analysis of antigen-antibody profiles can be done in a reliable and sensitive manner using a recently developed proteomics technology: protein G Dynabeads combined with a ProteinChip system based on SELDI-TOF (=surface enhanced laser desorption/ionization-time of flight) mass spectrometry (MS) or Maldi-TOF or ESI-MSMS. The magnetic beads are designed to capture immunoglobulins via a cell wall component, binding a wide range of IgG antibodies during incubation with various body fluids, such as sera. During a subsequent incubation with homogenized antigens it is possible to capture relevant antigens by secondary binding to the antibodies. After elution antigens can be analyzed by SELDI-TOF MS using ProteinChips with different, separating chip surfaces e.g. cationic and anionic exchangers, hydrophobic surfaces and metal-ion affinity-chromatographic surfaces. Resulting mass spectra can be statistically analyzed and compared to gain significantly higher or lower antigen-antibody-reactivity peaks according to the study groups. The identification of potential biomarkers will be done using highly sensitive MALDI-TOF/TOF (=matrix assisted laser desorption/ionization-time of flight) MS.

Protagen Arrays

For the analysis of antibody patterns and identification of potential autoantibody biomarker candidates we chose a highly sensitive antigen microarray, which is a promising approach in this field of interest. This method has already been successfully used for the discovery of autoantibodies targeting prostate cancer specific biomarkers and to screen sera of patients with, e.g. different pathological subtypes of multiple sclerosis or autoimmune hepatitis for autoreactive antibodies. To screen autoantibody reactivities in study sera we used an advanced high density microarray approach. Sera of patients before treatment with lucentis (n=10) were compared with sera of the same patients after treatment with lucentis (n=10). Two pools of ten sera each were created for each group, which were incubated on nitrocellulose-coated slides with 3800 immobilized randomly selected human proteins from the UNIclone® library (UNIchip®, Protagen, Dortmund, Germany) as described below. Incubation and washing steps were performed at 4° C. on an orbital shaker (Micromix 5, DPC, Los Angeles, Calif., USA). Slides were covered with one-pad FAST-frame hybridization chambers (Whatman, Maidstone, UK) and blocked with PBS containing 0.5% BSA for one hour. Afterwards slides were washed three times ten minutes each time with PBS containing 0.5% Tween 20 (PBS-T). Patients' sera were diluted 1:375 in PBS and incubated on the Protagen-Slides overnight. After three washing steps with PBS-T, each time for ten minutes, slides were treated with fluorescence labeled secondary antibody (1:500 diluted in PBS, goat anti-human IgG, Jackson ImmunoResearch Laboratories, West Grove, USA) for one hour in the dark. After three final washing steps, two with PBS-T and one with HPLC-grade ultra pure Water (ten minutes each time) slides were dried under vacuum. By using a high sensitive laser microarray scanner 16-bit TIFF (Tagged Information File Format) were generated. Spot intensities were quantified with ImaGene Software (ImaGene 5.5, Biodiscovery, CA, USA). After data normalization to internal standards with algorithm provided by Protagen, group differences were calculated and compared. For visualization of the resultant antigen-antibody complexes, slides were treated with a secondary fluorescence labeled antibody (Dylight 650) followed by confocal laser scanning. After data normalization spot intensities were compared and group differences were analyzed.

Analysis

Blood samples will be centrifuged at 1000 g for ten minutes and the supernatant will be stored at −80° C. for subsequent analysis. Magnetic protein G beads (Dynal, Oslo, Norway) will be incubated with the patient's sera. After several washings steps the patient's antibodies will be covalently bound to the beads using ethanolamine. The bead-antibody complexes will be incubated with homogenized retinal antigens. The antigens bound to the patient's autoantibodies will be eluted, concentrated, and analyzed by SELDI time-of-flight (TOF) MS ProteinChips with two different chromatographic surfaces (CM10 cation exchange and H50 reversed phase). The samples will be measured with a SELDI-TOF MS ProteinChip system (Biorad, Hercules) on a PBS-IIc ProteinChip Reader. Raw data will be transferred to CiphergenExpress 2.1 database software (Biorad, Hercules) for workup and analysis. A recently developed Proteomics Software Project (PSP) will statistically evaluate the spectra using different statistical approaches (trained neuronal networks, tree algorithms and multivariate statistics) to guarantee a high specificity and sensitivity of antibody patterns for the observed study groups. The PSP will additionally search for highly significant biomarkers directing a Statistical based analysis using above mentioned algorithms. The identification of biomarkers will be done by MALDI-TOF/TOF MS analysis. We aim to generate at least eight highly specific biomarkers (significance level $\alpha=0.05$ and power $(1-\beta)=90\%$) for "wet" AMD.

Statistical calculations of sample sizes were conducted in close cooperation with the Institute of Medical Biometry, Epidemiology and Informatics (IMBEI) at the University in Mainz and are also based on experiences from previous studies: the calculated number of cases (25) is sufficient to detect an effect on the serum antibody profiles, given a significance level $\alpha=0.05$ and power $(1-\beta)=90\%$. The statistical analysis will demonstrate if the antibody composition against retinal antigens within sera changes. A comparison to the control group will show if the modifications are beneficial, i.e. the serum compositions become more similar to the serum of healthy subjects, or not. A subsequent biomarker identification using MALDI-TOF/TOF MS (Bruker) may reveal valuable hints on the systemic effects.

After electrophoretic separation, proteins will be typically digested, crystallized on matrix, and analyzed on a MALDI target. The obtained peptide mass fingerprint data, will be exported into BioTools and used for an internal Mascot database search (SwissProt and NCBI), leading to protein identifications.

Antigen Microarrays

In this study, we used highly purified proteins, purchased at Sigma-Aldrich (Germany) and BioMol (Hamburg, Germany), as antigens. The antigen selection is based on previous autoantigen identifications in glaucoma patients by our group and survey of literature related to identifications of autoantigens in autoimmune diseases. Antigens were diluted to 1 µg/µl with PBS buffer optionally containing 1.5% Trehalose for optimal printing conditions. The spotting of antigens was performed with both a non-contact printing technology (sciFLEXARRAYER S3, Scienion, Berlin, Germany), based on piezo dispensing, and the commonly used pin based contact printing technique (OmniGrid100, Digilab Genomic Solutions, Ann Arbor, USA). Results were comparatively evaluated for spot morphology and spot to spot variability. For printing of the whole set of study microarrays the piezo based spotting technique was used. Each antigen was spotted in triplicate onto nitrocellulose-slides (Oncyte, nitrocellulose 16 multi-pad slides, Grace Bio-Labs, Bend, USA). As a positive and negative control we used mouse anti human IgG/A/M or human IgG (10 µg/µl) and spotting buffer. The spotting process was performed at RT and a humidity of 30%. Approximately 1 nl of each antigen-dilution was applied onto the nitrocellulose surface by spotting three times 330 pl on exactly the same position. The accurateness of the spotting volume and the correct positioning of the droplets were monitored prior and after the spotting process of each antigen using the sciDrop-VOLUME and autodrop-detection software (Scienion, Berlin, Germany).

Incubation and washing steps were performed at 4° C. on an orbital shaker (Titramax 100, Heidolph, Schwabach, Germany). Slides were covered with 16-pad FAST frame hybridization chambers (Whatmann, Maidstone, UK) and blocked with PBS containing 4% BSA or the Super G blocking buffer (Grace Biolabs) for one hour. Afterwards slides were washed three times with PBS containing 0.5% Tween (PBS-T). Patient sera were diluted 1:250 in PBS and aqueous humor in a ratio of 1:10 in PBS. 100-120 µl of these dilutions were randomly incubated on prepared antigen-slides overnight. After several washing steps with PBS-T, slides were incubated with a fluorescent Cy-5 labeled secondary antibody (1:500 diluted in PBS-T, goat anti-human IgG, Jackson ImmunoResearch Laboratories, West Grove, USA) for one hour in the dark. Two washing steps with PBS-T were followed by two final washing steps with HPLC-grade water. All microarrays were air dried before scanning, using a microarray scanner (Affymetrix 428 TM Array Scanner, High Wycombe, UK). Generated 16-bit TIFF images (Tagged Information File Format) of slides were analyzed using the Spotfinder 3.1.1 software (TM4, Dana-Faber Cancer Institute, Boston, USA) or ImaGene5 software. Background subtraction was performed according to the formula: spot intensity=mean intensity SP−((sumbkg−sumtop5bkg)/(number of pixelSP−number of pixelstop5bkg)) where SP represents any spot, bkg the corresponding background and top5bkg the top five percent of background pixel. The coefficient of variance (CV) was calculated as follows: CV=SDSP3/meanSPX . . . SPn, where SDSP3 represents the standard deviation across three replicate spots of one antigen of one sample, and meanSPX . . . SPn the mean of all spot intensities.

Example

An artificial neural network was performed prior to the analysis in a study cohort as described above. The autoantibody reactivities were analysed as described above.

These intensity values of antibody reactivities have been normalized and a calculation of the percentage difference of intensity values to reference values was calculated.

Based on the algorithm from the artificial neural network, an individual scoring was performed for a single patient, which has not been included prior to this analysis in the training (calculation) of the artificial neural network.

The different autoimmune reactivates were analysed for patient #22928 (from the study) in 1 µl of sera and used as input to the data mining algorithm trained prior to the study.

For this individual patient, the confidence levels was calculated as 0.0087 (−1: vision loss); 0.156 (0: no vision change) and 0.835 (1: vision gain). Thus, based on autoreactivity, the patient will respond to the anti-VEGF treatment with highest probability.

While there are shown and described presently preferred embodiments of the invention, it is to be distinctly understood that the invention is not limited thereto but may be otherwise variously embodied and practiced within the scope of the following claims.

The invention claimed is:

1. A method of treating an individual with wet AMD, the method comprising:
  (i) obtaining a sample from an individual having wet AMD;
  (ii) determining the quantity of at least one autoantibody selected from Group A antibodies directed against self antigen selected from the group consisting of opioid growth factor receptor (OGFR), mitogen-activated protein kinase 3 (MAPK3), Poly(rC)binding protein 2 (PolyRp2), Chromosome 17 (open reading frame 56), eukaryotic initiation factor 4A-1 (EIFA 4A-1), glutathione peroxidase 4 (GPX4), signal recognition particle 14 kDa protein (SPR14), Gamma-synuclein, histadine tRNA ligase (Jo-1), Pre-Albumin (transthyretin), glycerol-3-phosphate dehydrogenase (GPD2), AP-1 complex subunit mu-1 (AP1M1), alpha enolase (ENO1-H7), plasticity-related gene 2 (PRG2), ATP synthase, Guanine nucleotide binding protein subunit 1 (GNB 1-A3), tubulin beta-3 chain (TUBB3), heat shock protein 60 (HSP 60), islet cell autoantigen 1 (ICA1), selenoprotein O (SELO}, superoxidase dismutase (SOD), and gamma-enolase (ENO2);
  (iii) identifying the individual as a VEGF antagonist responder if the sample has an amount of the at least one autoantibody selected from Group A antibodies that has increased by at least 10% or decreased by at least 10% compared to a control; and
  (iv) administering a VEGF antagonist to the identified individual.

2. The method of claim 1, wherein the at least one autoantibody is selected from a subgroup A-1 of the group A antibodies directed against self antigen selected from the group consisting of OGFR, MAPK3, SRP14, ENO2, SOD, Pre-Albumin, Jo-1, PolyRp2, Chromosome 17, and EIFA 4A-1.

3. The method of claim 1, wherein the identifying step further comprises identifying the individual as a VEGF antagonist responder if the sample has an amount of the at least one autoantibody selected from Group A antibodies that has increased by at least 20% or decreased by at least 20% compared to a control.

4. The method of claim 1, wherein determining the quantity of at least one autoantibody is done using microarrays, lateral flow assay, microfluidic, or bead-based assays.

5. The method of claim 1, wherein determining the quantity of at least one autoantibody is done using radioimmunoassay, real-time PCR, mass spectrometry, Western blot assay, immunoblot assay or enzyme-linked immunoabsorbent assays (ELISA).

6. The method according to claim 1, wherein the sample is a fluid sample.

7. The method according to claim 6, wherein the fluid sample is blood, serum, tears, saliva, urine, a buccal cell sample, aqueous humor, or vitreous fluid.

8. The method according to claim 1, wherein the at least one antibody is selected from the group of antibodies directed against self antigen selected from the group consisting of OGFR, MAPK3, PolyRp2, Chromosome 17, EIFA 4A-1, GPX4, SRP14, Gamma-synuclein, Jo-1, Pre-Albumin, GPD2, AP1M1, and ENO1-H7.

9. The method according to claim 1, wherein the at least one antibody is selected from the group of antibodies directed against self antigen selected from the group consisting of OGFR, PolyRp2, Gamma-synuclein, Pre-Albumin, PRG2, GNB1-A3, and TUBB3.

10. The method according to claim 1, wherein the at least one antibody is selected from the group of antibodies directed against self antigen selected from the group consisting of OGFR, SPR14, and Pre-Albumin.

11. The method according to claim 1, wherein the at least one antibody is directed against OGFR.

* * * * *